(12) United States Patent
Richardson et al.

(10) Patent No.: US 9,821,049 B2
(45) Date of Patent: *Nov. 21, 2017

(54) METHOD OF CONFERRING A PROTECTIVE IMMUNE RESPONSE TO NOROVIRUS

(71) Applicant: TAKEDA VACCINES, INC., Bozeman, MT (US)

(72) Inventors: Charles Richardson, Bozeman, MT (US); Thomas S. Vedvick, Federal Way, WA (US); Thomas R. Foubert, Bozeman, MT (US); Robert F. Bargatze, Bozeman, MT (US); William Tino, Athens, GA (US)

(73) Assignee: Takeda Vaccines, Inc., Cambridge, MA (US)

( * ) Notice: Subject to any disclaimer, the term of this patent is extended or adjusted under 35 U.S.C. 154(b) by 18 days.

This patent is subject to a terminal disclaimer.

(21) Appl. No.: 13/837,389

(22) Filed: Mar. 15, 2013

(65) Prior Publication Data

US 2013/0273147 A1    Oct. 17, 2013

Related U.S. Application Data

(63) Continuation of application No. 12/765,641, filed on Apr. 22, 2010, now abandoned, which is a continuation-in-part of application No. 12/678,813, filed as application No. PCT/US2008/076763 on Sep. 18, 2008.

(60) Provisional application No. 60/986,826, filed on Nov. 9, 2007, provisional application No. 60/973,389, filed on Sep. 18, 2007.

(51) Int. Cl.
   *A61K 39/125*    (2006.01)
   *A61K 39/12*     (2006.01)
   *A61K 39/00*     (2006.01)

(52) U.S. Cl.
   CPC ............ *A61K 39/12* (2013.01); *A61K 39/125* (2013.01); *A61K 2039/5258* (2013.01); *A61K 2039/543* (2013.01); *A61K 2039/55572* (2013.01); *A61K 2039/57* (2013.01); *C12N 2770/16034* (2013.01)

(58) Field of Classification Search
   CPC ........ A61K 2039/5258; A61K 2039/70; A61K 2039/55505; A61K 2039/55566; A61K 2039/541; A61K 2039/6081; A61K 48/00; A61K 9/1652; A61K 2039/55522; A61K 2039/55527; A61K 2039/55594; A61K 2039/57; A61K 2039/572; C07K 16/10; C07K 1/18; C12N 2720/12323; C12N 2720/12334; C12N 2740/11023; C12N 2740/16023; C12N 2760/00023; G01N 2333/08
   See application file for complete search history.

(56) References Cited

U.S. PATENT DOCUMENTS

| | | |
|---|---|---|
| 5,645,051 A | 7/1997 | Schultz et al. |
| 5,861,241 A | 1/1999 | Herrmann et al. |
| 5,953,727 A | 9/1999 | Maslyn et al. |
| 6,165,502 A | 12/2000 | Oleske et al. |
| 6,251,678 B1 | 6/2001 | Volkin et al. |
| 6,391,318 B1 | 5/2002 | Illum et al. |
| 6,491,919 B2 | 12/2002 | Crane |
| 6,572,862 B1 | 6/2003 | Estes et al. |
| 6,602,697 B1 | 8/2003 | Cook, III |
| 6,942,865 B2 | 9/2005 | Estes et al. |
| 7,067,638 B1 | 6/2006 | Takeda et al. |
| 7,481,997 B1 | 1/2009 | Hardy |
| 7,527,801 B2* | 5/2009 | Coit ...................... A61K 39/12 424/184.1 |
| 7,955,603 B2 | 6/2011 | Richardson et al. |
| 8,119,145 B2 | 2/2012 | Coit et al. |
| 8,124,104 B2 | 2/2012 | Coit et al. |
| 8,142,793 B2 | 3/2012 | Coit et al. |
| 8,431,116 B2 | 4/2013 | Richardson et al. |
| 8,980,275 B2 | 3/2015 | Steadman et al. |
| 9,272,028 B2 | 3/2016 | Richardson et al. |
| 9,308,249 B2 | 4/2016 | Richardson et al. |
| 9,518,096 B2 | 12/2016 | Richardson et al. |
| 2004/0063188 A1 | 4/2004 | Robinson et al. |
| 2004/0265377 A1 | 12/2004 | Seager |
| 2005/0152911 A1* | 7/2005 | Hardy ................. A61K 39/125 424/159.1 |
| 2005/0154053 A1 | 7/2005 | Rhijn et al. |
| 2005/0155113 A1 | 7/2005 | Hamilton et al. |
| 2005/0215501 A1 | 9/2005 | Lipford et al. |
| 2005/0260225 A1 | 11/2005 | Goldberg et al. |

(Continued)

FOREIGN PATENT DOCUMENTS

| | | |
|---|---|---|
| EP | 1186890 A1 | 3/2002 |
| EP | 2360175 A2 | 8/2011 |

(Continued)

OTHER PUBLICATIONS

LoBue et al. Vaccine, Jun. 2006, vol. 24, No. 24, pp. 5220-5234.*
Nicollier-Jamot et al. Vaccine 2004, vol. 22, pp. 1079-1086.*
Liu et al. J. Virol. 2009, vol. 83, No. 13, pp. 6963-6968.*
Chachu et al. PloSPathog 2008, vol. 4 (12) pp. 1-13. See Figs. 1-7.*
Ball et al. Gastroenterology 1999, vol. 117, pp. 40-48.*
Allen et al., "Analysis of Amino Acid Variation in the P2 Domain of the GII-4 Norovirus VP1 Protein Reveals Putative Variant-Specific Epitopes," PLOS One, vol. 3: e1485, 2008.
Ando et al., "Genetic Classification of 'Norwalk-like Viruses,'" The Journal of Infectious Diseases, vol. 181(Suppl 2): S336-S348, 2000.
Angioni, C.F., "Supplementary European Search Report," 9 pages, from European Patent Appl. No. 07853688.5, European Patent Office, The Hague, Netherlands (dated Sep. 22, 2010).

(Continued)

*Primary Examiner* — Bao Li
(74) *Attorney, Agent, or Firm* — Cooley LLP

(57) ABSTRACT

The present invention relates to vaccine compositions comprising Norovirus antigens and adjuvants, in particular, mixtures of monovalent VLPs and mixtures of multivalent VLPs, and to methods of conferring protective immunity to Norovirus infections in a human subject.

13 Claims, 5 Drawing Sheets

(56) References Cited

U.S. PATENT DOCUMENTS

| | | | |
|---|---|---|---|
| 2007/0207526 A1* | 9/2007 | Coit | A61K 39/12 435/91.1 |
| 2008/0299152 A1 | 12/2008 | Richardson et al. | |
| 2010/0150961 A1 | 6/2010 | Vedvick et al. | |
| 2010/0266636 A1 | 10/2010 | Richardson et al. | |
| 2011/0070260 A1 | 3/2011 | Baric et al. | |
| 2011/0182975 A1 | 7/2011 | Richardson et al. | |
| 2011/0195113 A1 | 8/2011 | Richardson et al. | |
| 2012/0093861 A1 | 4/2012 | Richardson et al. | |
| 2012/0156243 A1 | 6/2012 | Richardson et al. | |
| 2013/0273102 A1 | 10/2013 | Richardson et al. | |
| 2015/0023995 A1 | 1/2015 | Richardson et al. | |
| 2016/0000899 A1 | 1/2016 | Richardson et al. | |
| 2016/0008455 A1 | 1/2016 | Richardson et al. | |

FOREIGN PATENT DOCUMENTS

| | | |
|---|---|---|
| JP | 10-500847 A | 1/1998 |
| JP | 2002-508748 A | 3/2002 |
| JP | 2002-536340 A | 10/2002 |
| JP | 2005-200420 A | 7/2005 |
| JP | 2005-524674 A | 8/2005 |
| JP | 2005-525415 A | 8/2005 |
| JP | 2005-538939 A | 12/2005 |
| JP | 2006-502979 A | 1/2006 |
| JP | 2006-507800 A | 3/2006 |
| JP | 2006-516638 A | 7/2006 |
| JP | 2006-518748 A | 8/2006 |
| JP | 2007-145775 A | 6/2007 |
| JP | 2007-537137 A | 12/2007 |
| JP | 2008-511556 A | 4/2008 |
| JP | 2009-516529 A | 4/2009 |
| JP | 2010-505766 A | 2/2010 |
| JP | 2011-506264 A | 3/2011 |
| JP | 5476544 B | 4/2014 |
| WO | WO 92/16543 A1 | 10/1992 |
| WO | WO 93/21325 A1 | 10/1993 |
| WO | WO 98/50071 A1 | 11/1998 |
| WO | WO 00/79280 A1 | 12/2000 |
| WO | WO 2003/077942 A2 | 9/2003 |
| WO | WO 2003/078455 A2 | 9/2003 |
| WO | WO 2005/020889 A2 | 3/2005 |
| WO | WO 2005/030806 A2 | 4/2005 |
| WO | WO 2005/060966 A1 | 7/2005 |
| WO | WO 2006/044857 A2 | 4/2006 |
| WO | WO 2006/067632 A2 | 6/2006 |
| WO | WO 2006/086188 A2 | 8/2006 |
| WO | WO 2006/091517 A2 | 8/2006 |
| WO | WO 2006/097530 A2 | 9/2006 |
| WO | WO 2006/136566 A1 | 12/2006 |
| WO | WO 2007/053188 A2 | 5/2007 |
| WO | WO 2007/081447 A1 | 7/2007 |
| WO | WO 2007/081447 A2 | 7/2007 |
| WO | WO 2008/042789 A1 | 4/2008 |
| WO | WO 2010/017542 A1 | 8/2008 |
| WO | WO 2009/039229 A2 | 3/2009 |
| WO | WO 2013/009849 A1 | 1/2013 |

OTHER PUBLICATIONS

Ausar et al., "Conformational stability and disassembly of norwalk virus like particles: effect of pH and temperature," J. Biol. Chem., vol. 281: 19478-19488, 2006.

Baldrick et al., Safety evaluation of monophosphoryl lipid A (MPL): an immunostimulatory adjuvant. Regulatory Toxicology and Pharmacology 2002; vol. 35:398-413.

Baldridge et al., Monophosphoryl lipid A enhances mucosal and systemic immunity to vaccine antigens following intranasal administration. Vaccine 2000; vol. 18:2416-2425.

Ball et al., Oral Immunization with Recombinant Norwalk Virus-Like Particles Induces a Systemic and Mucosal Immune Response in Mice. Journal of Virology 1998; vol. 72(2): 1345-1353.

Ball et al., Recombinant Norwalk virus-like particles given orally to volunteers: phase I study. Gastroenterology 1999; vol. 117:40-48.

Baric et al., "Expression and Self-Assembly of Norwalk Virus Capsid Protein from Venezuelan Equine Encephalitis Virus Replicons," J. Virol. 76(6):3023-3030 (2002).

Bertolotti-Ciarlet et al., "Structural Requirements for the Assembly of Norwalk Virus-Like Particles," J. Virol. 76(8):4044-4055 (2002).

Bull et al., "Emergence of a New Norovirus Genotype II.4 Variant Associated with Global Outbreaks of Gastroenteritis," Journal of Clinical Microbiology, vol. 44: 327-333, 2006.

Cachia et al., "The use of synthetic peptides in the design of a consensus sequence vaccine for Pseudomonas aeruginosa," J. Pept. Res. 52(4):289-299 (1998).

Cao et al., "Structural Basis for the Recognition of Blood Group Trisaccharides by Norovirus," J. Virol. 81(11):5949-5957 (2007).

Carpenter et al., Rational design of stable lyophilized protein formulations: some practical advice, Pharmaceutical Research, vol. 14: 969-975, 1997.

Cheetham et al., "Binding patterns of human norovirus-like particles to buccal and intestinal tissues of gnotobiotic pigs in relation to A/H histo-blood group antigen expression," Journal of Virology, vol. 81: 3535-3544, 2007.

Chen et al., "X-ray structure of a native calicivirus: Structural insights into antigenic diversity and host specificity," Proc. Natl Acad. Sci. USA 103(21):8048-8053 (2006).

Childers et al., "Adjuvant activity of monophosphoryl lipid A for nasal and oral immunization with soluble or liposome-associated antigen," Infection and Immunity, vol. 68: 5509-5516, 2000.

Davis and Ileum, Absorption enhancers for nasal drug delivery. Clinical Pharmacokinetics 2003; vol. 42:1107-1128.

Estes et al., Norwalk Virus Vaccines: Challenges and Progress. The Journal of Infectious Disease 2000; vol. 181(Suppl 2): S367-373.

Fankhauser et al., "Molecular Epidemiology of "Norwalk-like viruses" in Outbreaks of Gastroenteritis in the United States," J. Infect. Dis. 178(6):1571-1578 (1998).

Foubert et al., "Preclinical Development of a Broad Spectrum Norovirus Vaccine," AAPS National Biotechnology Conference, http://abstracts.aapspharmaceutica.com/ExpoNBC09/CC/forms/attendee/index.aspx?content=session Info&sessionId=150 (2009).

Gray et al., Detection of immunoglobulin M (IgM), IgA, and IgG Norwalk virus-specific antibodies by indirect enzyme-linked immunosorbent assay with baculovirus-expressed Norwalk virus capsid antigen in adult volunteers challenged with Norwalk virus. Journal of Clinical Microbiology 1994; vol. 32:3059-3063.

Guerrero et al., Recombinant Norwalk Virus-Like Particles Administered Intranasally to Mice Induce Systemic and Mucosal (Fecal and Vaginal) Immune Responses. Journal of Virology 2001; vol. 75:9713-9722.

Han et al., Immune responses to bovine norovirus-like particles with various adjuvants and analysis of protection in gnotobiotic calves. Vaccine 2006; vol. 24:317-326.

Han et al., "Thermosensitive and mucoadhesive delivery systems of mucosal vaccines," Methods, vol. 38:106-111, 2006.

Hansman et al., Genetic and antigenic diversity among Noroviruses. Journal of General Virology 2006; vol. 87: 909-919.

Harrington et al., "Systemic, Mucosal, and Heterotypic Immune Induction in Mice Inoculated with Venezuelan Equine Encephalitis Replicons Expressing Norwalk Virus-Like Particles," J. Virol. 76(2):730-742 (2002).

Herbst-Kralovetz et al., "Norwalk virus-like particles as vaccines," Exp. Rev. Vaccines 9(3):299-307 (2010).

Huang et al., "Noroviruses Bind to Human ABO, Lewis, and Secretor Histo-Blood Group Antigens: Identification of 4 Distinct Strain-Specific Patterns," J. Infect. Dis. 188(1):19-31 (2003).

Hutson et al., Norovirus disease: changing epidemiology and host susceptibility factors. Trends in Microbiology 2004; vol. 12(6):279-287.

Hutson et al., "Norwalk Virus-Like Particle Hemagglutination by Binding to H Histo-Blood Group Antigens," J. Virol. 77(1):405-415 (2003).

Illum et al., Chitosan as a novel nasal delivery system for peptide drugs. Pharmaceutical Research 1994.; vol. 11:1186-1189.

Illum et al., Chitosan as a novel nasal delivery system for vaccines. Advanced Drug Delivery Reviews 2001; vol. 51:81-96.

(56) References Cited

OTHER PUBLICATIONS

Illum et al., Nasal drug delivery—possibilities, problems and solutions. Journal of Controlled Release 2003; vol. 87:187-198.
International Search Report, 2 pages, PCT appl. No. PCT/US2007/079929 (dated Mar. 11, 2008).
International Search Report, 3 pages, PCT appl. No. PCT/US2008/076763 (dated Jul. 15, 2009).
International Search Report, 3 pages, PCT appl. No. PCT/US2009/053249 (dated Dec. 14, 2009).
International Search Report, 3 pages, PCT appl. No. PCT/US2012/046222 (dated Oct. 2, 2012).
Jaimes et al., "Maturation and Trafficking Markers on Rotavirus-Specific B Cells during Acute Infection and Convalescence in Children," J. Virol 78:10967-10976 (2004).
Jiang et al., "Expression, Self-Assembly, and Antigenicity of the Norwalk Virus Capsid Protein," J. Virol. 66(11):6527-6532 (1992).
Jiang et al., "Norwalk virus genome cloning and characterization," Science 250:1580-1583 (1990).
Johnson et al., Multiple Challenge Study of Host Susceptibility to Norwalk Gastroenteritis in U.S. Adults. The Journal of Infectious Disease 1990; vol. 161: 18-21.
Kamata et al., "Increased Frequency of Surface IgA-Positive Plasma Cells in the Intestinal Lamina Propia and Decreased IgA Excretion in Hyper IgA (HIGA) Mice, a Murine Model of IgA Nephropathy with Hyperserum IgA," J. Immunol. 165:1387-1394 (2000).
Ligocyte Pharmaceuticals, "Ligocyte Pharmaceuticals initiates U.S. clinical trial of norovirus vaccine," http://www.ligocyte.com/news/documents/LIGOCYTE-PHARMACEUTICALS-4-3-2007.pdf, Apr. 3, 2007, 2 pages.
Lindell et al., "Molecular Epidemiology of Norovirus Infections in Stockholm, Sweden, during the Years 2000 to 2003: Association of the GGIIb Genetic Cluster with Infection in Children," Journal of Clinical Microbiology, vol. 43: 1086-1092, 2005.
Lindesmith et al., Cellular and humoral immunity following Snow Mountain virus challenge. Journal of Virology 2005; vol. 79(5): 2900-2909.
Lindesmith et al., Human susceptibility and resistance to Norwalk infection. Nature Medicine 2003; vol. 9(5): 548-553.
Lindesmith et al., "Mechanisms of GII.4 Norovirus Persistence in Human Populations," PLOS One, vol. 5: e31, 2008.
Lobue et al., "Alphavirus adjuvanted norovirus-like particle vaccines: heterologous, humoral, and mucosal immune responses protect against murine norovirus challenge," J. Virol., vol. 83(7): 3212-3227, 2009.
Lobue et al., Multivalent Norovirus vaccines induce strong mucosal and systemic blocking antibodies against multiple strains. Vaccine 2006; vol. 24(24): 5220-5234.
Malcolmson and Embleton, "Dry powder formulations for pulmonary delivery," Pharmaceutical Science and Technology Today, vol. 1:394-398, 1998.
Mason et al., "Expression of Norwalk virus capsid protein in transgenic tobacco and potato and its oral immunogenicity in mice," Proc. Natl Acad. Sci. USA 93(11):5335-5340 (1996).
Matsui et al., Immunity to Calicivirus infection. The Journal of Infectious Diseases 2000; vol.181(S2): S331-335.
McBurney et al., "Developing Broadly Reactive HIV-1/AIDS Vaccines: A Review of Polyvalent and Centralized HIV-1 Vaccines," Curr. Pharm. Design 13(19):1957-1964 (2007).
Mead et al., Food Related Illness and Death in the U.S., Emerging Infectious Diseases 1999; vol. 5(5): 607-635.
Muthumani et al "Immunogenicity of novel consensus-based DNA vaccines against Chikungunya virus," Vaccine 26(40):5128-5134 (2008).
Nicollier-Jamot et al., Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. Vaccine 2004; vol. 22:1079-1086.
Noel et al., Correlation of patient immune responses with genetically characterized small round-structured viruses involved in outbreaks of nonbacterial acute gastroenteritis in the United States, 1990 to 1995. Journal of Medical Virology 1997; vol. 53:372-383.
O'Hagan et al., "Recent developments in adjuvants for vaccines against infectious diseases," Biomol. Eng. 18(3):69-85 (2001).
Parrino et al., Clinical immunity in acute gastroenteritis caused by Norwalk agent. New England Journal of Medicine 1977; vol. 297:86-89.
Partial European Searcht Report, 7 pages, EP appl. No. 13157572.2 (dated Apr. 5, 2013).
Pelosi et al., "The Seroepidemiology of Genogroup 1 and Genogroup 2 Norwalk-Like Viruses in Italy," J. Med. Virol. 58:93-99 (1999).
Periwal et al., A Modified Cholera Holotoxin CT-E29H Enhances Systemic and Mucosal Immune Responses to Recombinant Norwalk Virus-like Particle Vaccine. Vaccine 2003; vol. 21:376-385.
Prasad et al., "Structural studies of recombinant norwalk capsids," J. Infect. Dis., vol. 181(s2), S317-S321, 2000.
Rasmussen et al., "In Multiple Myeloma Clonotypic $CD38^-/CD19^+/CD27^+$ Memory B Cells Recirculate Through Bone Marrow, Peripheral Blood and Lymph Nodes," Leuk. Lymph. 45(7):1413-1417 (2004).
Richardson et al., "Norovirus Vaccine Formulations," U.S. Appl. No. 12/816,495, filed Jun. 16, 2010.
Sha et al., "Activation of Airway Epithelial Cells by Toll-Like Receptor Agonists," Am. J. Respir. Cell Mol. Biol. 31(3):358-364 (2004).
Siebenga et al., "Epochal Evolution of GGII.4 Norovirus Capsid Proteins from 1995 to 2006," Journal of Virology, vol. 81: 9932-9941, 2007.
Singh et al., "A preliminary evaluation of alternative adjuvants to alum using a range of established and new generation vaccine antigens," Vaccine 24(10):1680-1686 (2006).
Souza et al., "A human norovirus-like particle adjuvanted with ISCOM or mLT induces cytokine and antibody responses and protection to the homologous GII.4 human norovirus in a gnotobiotic pig disease model," Vaccine, vol. 25: 8448-8459, 2007.
Supplementary European Search Report, 13 pages, EP appl. No. 08832560.0 (dated Apr. 5, 2012).
Supplementary European Search Report, 8 pages., EP appl. No. 09805653.4 (dated Dec. 2, 2011).
Tacket et al., Humoral, mucosal, and cellular immune response to oral Norwalk virus-like particles in volunteers. Clinical Immunology 2003; vol. 108: 241-247.
Tacket et al., "Human immune responses to a novel norwalk virus vaccine delivered in transgenic potatoes.," J. Infect. Dis., vol. 182(1): 302-305, 2000.
Ugwoke et al., "Nasal mucoadhesive drug delivery: Background, applications, trends and future perspectives," Advanced Drug Delivery Reviews, vol. 57: 1640-1665, 2005.
Wang et al., "Effective synthetic peptide vaccine for foot-and-mouth disease in swine," Vaccine 20(19-20):2603-2610 (2002).
Written Opinion of the International Searching Authority, 4 pages, PCT appl. No. PCT/US2007/079929 (dated Mar. 11, 2008).
Written Opinion of the International Searching Authority, 5 pages, PCT appl. No. PCT/US2008/076763 (dated Jul. 15, 2009).
Written Opinion of the International Searching Authority, 7 pages, PCT appl. No. PCT/US2Q09/053249 (dated Dec. 14, 2009).
Written Opinion of the International Searching Authority, 6 pages, PCT appl. No. PCT/US2012/046222 (dated Oct. 2, 2012).
Wyatt et al., Comparison of three agents of acute infectious nonbacterial gastroenteritis by cross-challenge in volunteers. Journal of Infecious. Diseases 1974.; vol. 129:709-714.
Xia et al., "Norovirus Capsid Protein Expressed in Yeast Forms Virus-like Particles and Stimulates Systemic and Mucosal Immunity in Mice Following an Oral Administration of Raw Yeat Extracts," J. Med Virol. 79:74-83 (2007).
U.S. Appl. No. 13/330,854, filed Dec. 20, 2011.
U.S. Appl. No. 13/837,653, filed Mar. 15, 2013.
U.S. Appl. No. 13/836,446, filed Mar. 15, 2013.
U.S. Appl. No. 13/837,885, filed Mar. 15, 2013.

(56) References Cited

OTHER PUBLICATIONS

U.S. Appl. No. 12/678,813, filed Jul. 6, 2010.
U.S. Appl. No. 13/023,363, filed Feb. 8, 2011.
U.S. Appl. No. 13/840,403, filed Mar. 15, 2013.
MMWR, 2011, Updated Norovirus Outbreak Management and Disease Prevention Guidelines, 20 pages. [https://www.cdc.gov./mmwr/preview/mmwrhtml/rr6003a1.htm] downloaded May 1, 2017.
Baldridge et al., "Taking a Toll on human disease: Toll-like receptor 4 agonists as vaccine adjuvants and monotherapeutic agents," Exp. Opin. Biol. Ther. 4(7):1129-1138 (2004).
Bok et al., "Chimpanzees as an animal model for human norovirus infection and vaccine development," Proc. Natl. Acad. Sci. USA 108(1):325-330 (2011).
Broadbent and Subbarao, "Influenza virus vaccines: lessons from the 2009 H1N1 pandemic," Curr. Opin. Virol. 1:254-262 (2011).
Cuellar et al., "Size and mechanical stability of norovirus capsids depend on pH: a nanoindentation study," J. Gen. Virol. 91:2449-2456 (2010).
Da Silva et al., "Adsorption and Aggregation Properties of Norovirus GI and GII Virus-like Particles Demonstrate Differing Responses to Solution Chemistry," Environ. Sci. Technol. 45(2):520-526 (2011).
Dagan et al., "Reduced Response to Multiple Vaccines Sharing Common Protein Epitopes That Are Administered Simultaneously to Infants," Infect. Immun. 66(5):2093-2098 (1998).
Extended European Search Report, EP appl. No. 13157572.2, 9 pages (dated Jul. 23, 2013).
Extended European Search Report, EP appl. No. 13157573.0, 6 pages (dated Apr. 5, 2013).
Extended European Search Report, EP appl. No. 13173005.3, 5 pages (dated Jul. 16, 2013).
Frey et al., "Interference of Antibody Production to Hepatitis B Surface Antigen in a Combination Hepatitis A/Hepatitis B Vaccine," J. Infect. Dis. 180:2018-2022 (1999).
Giannini et al., "Enhanced humoral and memory B cellular immunity using HPV16/18 L1 VLP vaccine formulated with the MPL/aluminium salt combination (AS04) compared to aluminium salt only," Vaccine 24: 5937-5949 (2006).
Glass, R.I., et al. "Norovirus gastroenteritis." New England Journal of Medicine (2009); 361.18: 1776-1785.
Guy et al., "Evaluation of Interferences between Dengue Vaccine Serotypes in a Monkey Model,"Am. J. Trop. Med. Hyg. 80(2):302-311 (2009).
Hardy, Michele E., "Norovirus protein structure and function", FEMS Microbiology (2005); 253: 1-8.
Kawana et al., "A surface immunodeterminant of human papillomavirus type 16 minor capsid protein L2." Virology (1998); 245.2: 353-359.
Larke et al., "Combined single-clade candidate HIV-1 vaccines induce T cell responses limited multiple forms of in vivo immune interference," Eur. J. Immunol. 37:566-577 (2007).
Lew et al., "Molecular Characterization and Expression of the Capsid Protein of a Norwalk-like Virus Recovered from a Desert Shield Troop with Gastroenteritis," Virol. 319-325 (1994).
Lin, S.W., et al. "Intramuscular rather than oral administration of replication-defective adenoviral vaccine vector induces specific CD8+ T-cell responses in the gut." Vaccine (2007); 25(12): 2187-2193.
Martin et al., "Role of Innate Immune Factors in the Adjuvant Activity of Monophosphoryl Lipid A," Infect. Immun. 71(5):2498-2507 (2003).
Oliver, S. L., et al. "Genotype 1 and genotype 2 bovine noroviruses are antigenically distinct but share a cross-reactive epitope with human noroviruses." Journal of Clinical Microbiology (2006); 44.3: 992-998.
Parra and Green, "Sequential Gastroenteritis Episodes Caused by 2 Norovirus Genotypes," Emerg. Infect. Dis. 20(6):1016-1018 (2014).
Pastrana et al., "Cross-neutralization of cutaneous and mucosal Papillomavirus types with anti-sera to the amino terminus of L2." Virology (2005); 337.2: 365-372.
Reagan-Shaw et al., "Dose translation from animal to human studies revisited," FASEB J. 22:659-661 (2007).
Richardson et al., "Norovirus virus-like particle vaccines for the prevention of acute gastroenteritis," Expert Rev. Vaccines 12(2):155-167 (2013).
Supplementary European Search Report, EP Appl. No. 12811916.1, 8 pages (dated Feb. 20, 2015).
Zhang et al., "Trivalent Human Papillomavirus (HPV) VLP vaccine covering HPV type 58 can elicit high level of humoral immunity but also induce immune interference among component types," Vaccine 28:3479-3487 (2010).
Zheng et al., "Norovirus classification and proposed strain nomenclature," Virology 346:312-323 (2006).
Song, Wei, et al., "Research Progress on Molecular Biology Feature of Noroviruses and its Subunit Vaccine." Journal of Agricultural Science and Technology (2010); 12(6): 43-48.
Clark and Offit, "Vaccines for rotavirus gastroenteritis universally needed for infants." Pediatric Annals (2004); 33(8): 537-543.
Kitamoto et al., "Cross-Reactivity among Several Recombinant Calicivirus Virus-Like Particles (VLPs) with Monoclonal Antibodies Obtained from Mice Immunized Orally with One Type of VLP." J. Clin. Microbiol. (2002); 40(7): 2459-2465.
Midthun and Kapikian. "Rotavirus vaccines: an overview." Clinical Microbiology Reviews (1996); 9(3): 423-434.
Nakata, S., "Vaccine development for Norwalk Virus." Nippon Rinsho (2002); 60(6): 1222-1227 (with English Abstract and English translation), 12 pages.
Notice of Opposition in European Patent No. EP 2601970 (Application No. EP 13157573.0), filed Jul. 21, 2017, 40 pages.

\* cited by examiner

A.

B.

A.

B.

METHOD OF CONFERRING A PROTECTIVE IMMUNE RESPONSE TO NOROVIRUS

CROSS-REFERENCE TO RELATED APPLICATIONS

This application is a continuation of U.S. patent application Ser. No. 12/765,641, filed Apr. 22, 2010, which is a continuation-in-part of U.S. patent application Ser. No. 12/678,813, filed Mar. 18, 2010, which is a national stage application of International Application No. PCT/US2008/076763, filed Sep. 18, 2008, which claims the benefit of priority of U.S. Provisional Application No. 60/973,389, filed Sep. 18, 2007, and U.S. Provisional Application No. 60/986,826, filed Nov. 9, 2007, all of which are herein incorporated by reference in their entireties.

STATEMENT OF GOVERNMENT SUPPORT

This invention was produced with government support from the US Army Medical Research and Material Command, under contract number W81XWH-05-C-0135. The government may have certain rights to the invention.

FIELD OF THE INVENTION

The invention is in the field of vaccines, particularly vaccines for Noroviruses. In addition, the invention relates to methods of preparing vaccine compositions and methods of inducing a protective immune response.

BACKGROUND OF THE INVENTION

Noroviruses are non-cultivatable human Caliciviruses that have emerged as the single most important cause of epidemic outbreaks of nonbacterial gastroenteritis (Glass et al., 2000; Hardy et al., 1999). The clinical significance of Noroviruses was under-appreciated prior to the development of sensitive molecular diagnostic assays. The cloning of the prototype genogroup I Norwalk virus (NV) genome and the production of virus-like particles (VLPs) from a recombinant Baculovirus expression system led to the development of assays that revealed widespread Norovirus infections (Jiang et al. 1990; 1992).

Noroviruses are single-stranded, positive sense RNA viruses that contain a non-segmented RNA genome. The viral genome encodes three open reading frames, of which the latter two specify the production of the major capsid protein and a minor structural protein, respectively (Glass et al. 2000). When expressed at high levels in eukaryotic expression systems, the capsid protein of NV, and certain other Noroviruses, self-assembles into VLPs that structurally mimic native Norovirus virions. When viewed by transmission electron microscopy, the VLPs are morphologically indistinguishable from infectious virions isolated from human stool samples.

Immune responses to Noroviruses are complex, and the correlates of protection are just now being elucidated. Human volunteer studies performed with native virus demonstrated that mucosally-derived memory immune responses provided short-term protection from infection and suggested that vaccine-mediated protection is feasible (Lindesmith et al. 2003; Parrino et al. 1997; Wyatt et al., 1974).

Although Norovirus cannot be cultivated in vitro, due to the availability of VLPs and their ability to be produced in large quantities, considerable progress has been made in defining the antigenic and structural topography of the Norovirus capsid. VLPs preserve the authentic confirmation of the viral capsid protein while lacking the infectious genetic material. Consequently, VLPs mimic the functional interactions of the virus with cellular receptors, thereby eliciting an appropriate host immune response while lacking the ability to reproduce or cause infection. In conjunction with the NIH, Baylor College of Medicine studied the humoral, mucosal and cellular immune responses to NV VLPs in human volunteers in an academic, investigator-sponsored Phase I clinical trial. Orally administered VLPs were safe and immunogenic in healthy adults (Ball et al. 1999; Tacket et al. 2003). At other academic centers, preclinical experiments in animal models have demonstrated enhancement of immune responses to VLPs when administered intranasally with bacterial exotoxin adjuvants (Guerrero et al. 2001; Nicollier-Jamot et al. 2004; Periwal et al. 2003; Souza et al. (2007) Vaccine, doi: 10.1016/j.vaccine.2007.09.040). However, no studies have reported being able to achieve protective immunity against Norovirus using any Norovirus vaccine.

SUMMARY OF THE INVENTION

The present invention provides methods of inducing protective immunity to a Norovirus infection in a subject, in particular a human subject, comprising administering a vaccine comprising at least one Norovirus antigen. In one embodiment, the antigen is a Norovirus virus-like particle (VLP). Vaccines used in the methods of the invention may further comprise one or more adjuvants. The Norovirus VLPs can be selected from genogroup I or genogroup II virus or a mixture thereof. In one embodiment, the vaccine comprises Norovirus VLPs in a concentration from about 0.01% to about 80% by weight. In another embodiment, the vaccine comprises dosages of Norovirus VLPs from about 1 µg to about 100 mg per dose. In certain embodiments, the vaccine comprises a dosage of Norovirus VLPs of about 25 µg, about 30 µg, about 50 µg, about 60 µg, about 70 µg, about 80 µg, about 90 µg, about 100 µg, about 125 µg, or about 150 µg.

In some embodiments, the vaccine further comprises a delivery agent, which functions to enhance antigen uptake, provide a depot effect, increase antigen retention time at the site of delivery, or enhance the immune response through relaxation of cellular tight junctions at the delivery site. The delivery agent can be a bioadhesive, preferably a mucoadhesive selected from the group consisting of dermatan sulfate, chondroitin, pectin, mucin, alginate, cross-linked derivatives of poly(acrylic acid), polyvinyl alcohol, polyvinyl pyrollidone, polysaccharides, hydroxypropyl methylcellulose, lectins, fimbrial proteins, and carboxymethylcellulose. Preferably, the mucoadhesive is a polysaccharide. More preferably, the mucoadhesive is chitosan, or a mixture containing chitosan, such as a chitosan salt or chitosan base.

In other embodiments, the vaccine comprises an adjuvant. The adjuvant may be selected from the group consisting of toll-like receptor (TLR) agonists, monophosphoryl lipid A (MPL®), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, endotoxins, for instance bacterial endotoxins and liposomes. Preferably, the adjuvant is a toll-like receptor (TLR) agonist.

More preferably, the adjuvant is MPL®. In certain embodiments, the vaccine comprises two adjuvants, such as MPL® and alum.

The methods of the present invention include administering Norovirus vaccines formulated as a liquid or a dry powder. Dry power formulations may contain an average particle size from about 10 to about 500 micrometers in diameter. Suitable routes for administering the vaccine include mucosal, intramuscular, intravenous, subcutaneous, intradermal, subdermal, or transdermal. In particular, the route of administration may be intramuscular or mucosal, with preferred routes of mucosal administration including intranasal, oral, or vaginal routes of administration. In another embodiment, the vaccine is formulated as a nasal spray, nasal drops, or dry powder, wherein the vaccine is administered by rapid deposition within the nasal passage from a device containing the vaccine held close to the nasal passageway. In another embodiment, the vaccine is administrated to one or both nostrils. In still another embodiment, the vaccine is administered intramuscularly.

DETAILED DESCRIPTION OF THE INVENTION

Figure 1:
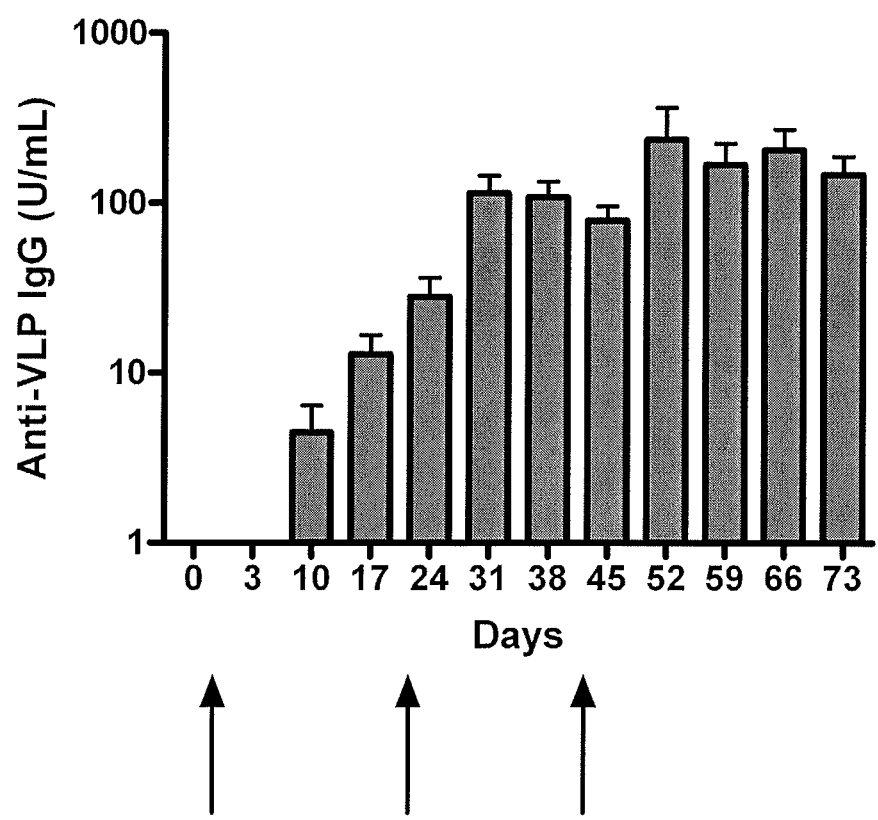
FIG. 1 shows that Norwalk Virus (NV)-specific IgG is elicited in rabbits immunized with dry powder VLPs. Rabbits were dosed 3 times, via the intranasal route of administration, on days 1, 22 and 43 (arrows) with 50 μg NV-VLP+50 μg MPL. Serum from each rabbit was tested for NV-VLP-specific IgG by ELISA on the days indicated. Only the VLP vaccinated rabbits had NV-VLP-specific IgG, whereas the untreated and placebo treatment groups had no detectable antigen-specific antibodies (data not shown). Arithmetic means of the responses are shown and expressed in U/mL (1 U~1 μg). Bars indicate the standard error of the mean.

The present invention relates to methods of eliciting a protective immunity to Norovirus infections in a subject. In particular, the present invention provides methods of administering a vaccine comprising Norovirus VLPs and at least one adjuvant to a human, wherein the vaccine confers protection from at least one symptom of Norovirus infection. Additionally or alternatively, the vaccine may further comprise at least one delivery agent.

Norovirus Antigens

The invention provides a composition comprising one or more Norovirus antigens. By "Norovirus," "Norovirus (NOR)," "norovirus," and grammatical equivalents herein, are meant members of the genus Norovirus of the family Caliciviridae. In some embodiments, a Norovirus can include a group of related, positive-sense single-stranded RNA, nonenveloped viruses that can be infectious to human or non-human mammalian species. In some embodiments, a Norovirus can cause acute gastroenteritis in humans. Noroviruses also can be referred to as small round structured viruses (SRSVs) having a defined surface structure or ragged edge when viewed by electron microscopy. Included within the Noroviruses are at least four genogroups (GI-IV) defined by nucleic acid and amino acid sequences, which comprise 15 genetic clusters. The major genogroups are GI and GII. GIII and GIV are proposed but generally accepted. Representative of GIII is the bovine, Jena strain. GIV contains one virus, Alphatron, at this time. For a further description of Noroviruses see Vinje et al. J. Clin. Micro. 41:1423-1433 (2003). By "Norovirus" also herein is meant recombinant Norovirus virus-like particles (rNOR VLPs). In some embodiments, recombinant expression of at least the Norovirus capsid protein encoded by ORF2 in cells, e.g., from a baculovirus vector in Sf9 cells, can result in spontaneous self-assembly of the capsid protein into VLPs. In some embodiments, recombinant expression of at least the Norovirus proteins encoded by ORF1 and ORF2 in cells, e.g., from a baculovirus vector in Sf9 cells, can result in spontaneous self-assembly of the capsid protein into VLPs. VLPs are structurally similar to Noroviruses but lack the viral RNA genome and therefore are not infectious. Accordingly, "Norovirus" includes virions that can be infectious or non-infectious particles, which include defective particles.

Non-limiting examples of Noroviruses include Norwalk virus (NV, GenBank M87661, $NP_{06821}$), Southampton virus (SHV, GenBank L07418), Desert Shield virus (DSV, U04469), Hesse virus (HSV), Chiba virus (CHV, GenBank AB042808), Hawaii virus (HV, GenBank U0761 1), Snow Mountain virus (SMV, GenBank U70059), Toronto virus (TV, Leite et al., Arch. Virol. 141:865-875), Bristol virus (BV), Jena virus (JV, AJ01099), Maryland virus (MV, AY032605), Seto virus (SV, GenBank AB031013), Camberwell (CV, AF145896), Lordsdale virus (LV, GenBank X86557), Grimsby virus (GrV, AJ004864), Mexico virus (MXV, GenBank U22498), Boxer (AF538679), C59 (AF435807), VA115 (AY038598), BUDS (AY660568), Houston virus (HoV, AY502023), MOH (AF397156), Parris Island (PiV; AY652979), VA387 (AY038600), VA207 (AY038599), and Operation Iraqi Freedom (OIF, AY675554). The nucleic acid and corresponding amino acid sequences of each are all incorporated by reference in their entirety. In some embodiments, a cryptogram can be used for identification purposes and is organized: host species from which the virus was isolated/genus abbreviation/species abbreviation/strain name/year of occurrence/country of origin. (Green et al., Human Caliciviruses, in Fields Virology Vol. 1 841-874 (Knipe and Howley, editors-in-chief, 4th ed., Lippincott Williams & Wilkins 2001)). Norwalk virus, Snow Mountain virus, and Houston virus are preferred in some embodiments.

The Norovirus antigen may be in the form of peptides, proteins, or virus-like particles (VLPs). In a preferred embodiment, the Norovirus antigen comprises VLPs. As used herein, "virus-like particle(s) or VLPs" refer to a virus-like particle(s), fragment(s), aggregates, or portion(s) thereof produced from the capsid protein coding sequence of Norovirus and comprising antigenic characteristic(s) similar to those of infectious Norovirus particles. Norovirus antigens may also be in the form of capsid monomers, capsid multimers, protein or peptide fragments of VLPs, or aggregates or mixtures thereof. The Norovirus antigenic proteins or peptides may also be in a denatured form, produced using methods known in the art.

The VLPs of the present invention can be formed from either the full length Norovirus capsid protein such as VP1 and/or VP2 proteins or certain VP1 or VP2 derivatives using standard methods in the art. Alternatively, the capsid protein used to form the VLP is a truncated capsid protein. In some embodiments, for example, at least one of the VLPs comprises a truncated VP1 protein. In other embodiments, all the VLPs comprise truncated VP1 proteins. The truncation may be an N- or C-terminal truncation. Truncated capsid proteins are suitably functional capsid protein derivatives. Functional capsid protein derivatives are capable of raising an immune response (if necessary, when suitably adjuvanted) in the same way as the immune response is raised by a VLP consisting of the full length capsid protein.

VLPs may contain major VP1 proteins and/or minor VP2 proteins. In some embodiments, each VLP contains VP1 and/or VP2 protein from only one Norovirus genogroup giving rise to a monovalent VLP. As used herein, the term "monovalent" means the antigenic proteins are derived from a single Norovirus genogroup. For example, the VLPs contain VP1 and/or VP2 from a virus strain of genogroup I (e.g., VP1 and VP2 from Norwalk virus). Preferably the VLP is comprised of predominantly VP1 proteins. In one embodiment of the invention, the antigen is a mixture of monovalent VLPs wherein the composition includes VLPs comprised of VP1 and VP2 from a single Norovirus genogroup mixed with VLPs comprised of VP1 and VP2 from a different Norovirus genogroup (e.g. Norwalk virus and Houston virus) taken from multiple viral strains. Purely by way of example the composition can contain monovalent VLPs from one or more strains of Norovirus genogroup I together with monovalent VLPs from one or more strains of Norovirus genogroup II. Strains may be selected based on their predominance of circulation at a given time. Preferably, the Norovirus VLP mixture is composed of the strains of Norwalk and Houston Noroviruses. More preferably, the Norovirus VLP mixture is composed of the strains of Norwalk and a consensus sequence derived from genogroup II Noroviruses. Consensus sequences derived from circulating Norovirus sequences and VLPs made with such sequences are described in WO 2010/017542, which is herein incorporated by reference in its entirety.

However, in an alternative embodiment of the invention, the VLPs may be multivalent VLPs that comprise, for example, VP1 and/or VP2 proteins from one Norovirus genogroup intermixed with VP1 and/or VP2 proteins from a second Norovirus genogroup, wherein the different VP1 and VP2 proteins are not chimeric VP1 and VP2 proteins, but associate together within the same capsid structure to form immunogenic VLPs. As used herein, the term "multivalent" means that the antigenic proteins are derived from two or more Norovirus genogroups or strains. Multivalent VLPs may contain VLP antigens taken from two or more viral strains. Purely by way of example the composition can contain multivalent VLPs comprised of capsid monomers or multimers from one or more strains of Norovirus genogroup I (e.g. Norwalk virus) together with capsid monomers or multimers from one or more strains of Norovirus genogroup II (e.g. Houston virus). Preferably, the multivalent VLPs contain capsid proteins from the strains of Norwalk and Houston Noroviruses, or other predominantly circulating strains at a given time.

The combination of monovalent or multivalent VLPs within the composition preferably would not reduce the immunogenicity of each VLP type. In particular it is preferred that there is no interference between Norovirus VLPs in the combination of the invention, such that the combined VLP composition of the invention is able to elicit immunity against infection by each Norovirus genotype represented in the vaccine. Suitably the immune response against a given VLP type in the combination is at least 50% of the immune response of that same VLP type when measured individually, preferably 100% or substantially 100%. The immune response may suitably be measured, for example, by antibody responses, as illustrated in the examples herein.

Multivalent VLPs may be produced by separate expression of the individual capsid proteins followed by combination to form VLPs. Alternatively multiple capsid proteins may be expressed within the same cell, from one or more DNA constructs. For example, multiple DNA constructs may be transformed or transfected into host cells, each vector encoding a different capsid protein. Alternatively a single vector having multiple capsid genes, controlled by a shared promoter or multiple individual promoters, may be used. IRES elements may also be incorporated into the vector, where appropriate. Using such expression strategies, the co-expressed capsid proteins may be co-purified for subsequent VLP formation, or may spontaneously form multivalent VLPs which can then be purified.

A preferred process for multivalent VLP production comprises preparation of VLP capsid proteins or derivatives, such as VP1 proteins, from different Norovirus genotypes, mixing the proteins, and assembly of the proteins to produce multivalent VLPs. The VP1 proteins may be in the form of a crude extract, be partially purified or purified prior to mixing. Assembled monovalent VLPs of different genogroups may be disassembled, mixed together and reassembled into multivalent VLPs. Preferably the proteins or VLPs are at least partially purified before being combined. Optionally, further purification of the multivalent VLPs may be carried out after assembly.

Suitably the VLPs of the invention are made by disassembly and reassembly of VLPs, to provide homogenous and pure VLPs. In one embodiment multivalent VLPs may be made by disassembly of two or more VLPs, followed by combination of the disassembled VLP components at any suitable point prior to reassembly. This approach is suitable when VLPs spontaneously form from expressed VP1 protein, as occurs for example, in some yeast strains. Where the expression of the VP1 protein does not lead to spontaneous VLP formation, preparations of VP1 proteins or capsomers may be combined before assembly into VLPs.

Where multivalent VLPs are used, preferably the components of the VLPs are mixed in the proportions in which they are desired in the final mixed VLP. For example, a mixture of the same amount of a partially purified VP1 protein from Norwalk and Houston viruses (or other Norovirus strains) provides a multivalent VLP with approximately equal amounts of each protein.

Compositions comprising multivalent VLPs may be stabilized by solutions known in the art, such as those of WO 98/44944, WO 00/45841, incorporated herein by reference.

Compositions of the invention may comprise other proteins or protein fragments in addition to VP1 and VP2 proteins or derivatives. Other proteins or peptides may also be co-administered with the composition of the invention. Optionally the composition may also be formulated or co-administered with non-Norovirus antigens. Suitably these antigens can provide protection against other diseases.

The VP1 protein or functional protein derivative is suitably able to form a VLP, and VLP formation can be assessed by standard techniques such as, for example, electron microscopy and dynamic laser light scattering.

Antigen Preparation

The antigenic molecules of the present invention can be prepared by isolation and purification from the organisms in which they occur naturally, or they may be prepared by recombinant techniques. Preferably the Norovirus VLP antigens are prepared from insect cells such as Sf9 or H5 cells, although any suitable cells such as *E. coli* or yeast cells, for example, *S. cerevisiae, S. pombe, Pichia pastori* or other *Pichia* expression systems, mammalian cell expression such as CHO or HEK systems may also be used. When prepared by a recombinant method or by synthesis, one or more insertions, deletions, inversions or substitutions of the amino acids constituting the peptide may be made. Each of the aforementioned antigens is preferably used in the substantially pure state.

The procedures of production of norovirus VLPs in insect cell culture have been previously disclosed in U.S. Pat. No. 6,942,865, which is incorporated herein by reference in its entirety. Briefly, a cDNA from the 3' end of the genome containing the viral capsid gene (ORF2) and a minor structural gene (ORF3) were cloned. The recombinant baculoviruses carrying the viral capsid genes were constructed from the cloned cDNAs. Norovirus VLPs were produced in Sf9 or H5 insect cell cultures.

Adjuvants

The invention further provides a composition comprising adjuvants for use with the Norovirus antigen. Most adjuvants contain a substance designed to protect the antigen from rapid catabolism, such as aluminum hydroxide or mineral oil, and a stimulator of immune responses, such as *Bordetella pertussis* or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes; biodegradable microspheres; and Quil A.

Suitable adjuvants also include, but are not limited to, toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, oil-in-water emulsions, MF59, and squalene. In some embodiments, the adjuvants are not bacterially-derived exotoxins. Preferred adjuvants include adjuvants which stimulate a Th1 type response such as 3DMPL or QS21.

Monophosphoryl Lipid A (MPL), a non-toxic derivative of lipid A from *Salmonella*, is a potent TLR-4 agonist that has been developed as a vaccine adjuvant (Evans et al. 2003). In pre-clinical murine studies intranasal MPL has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; 2004). MPL stimulates the induction of innate immunity through the TLR-4 receptor and is thus capable of eliciting nonspecific immune responses against a wide range of infectious pathogens, including both gram negative and gram positive bacteria, viruses, and parasites (Baldrick et al. 2004; Persing et al. 2002). Inclusion of MPL in intranasal formulations should provide rapid induction of innate responses, eliciting nonspecific immune responses from viral challenge while enhancing the specific responses generated by the antigenic components of the vaccine.

Accordingly, in one embodiment, the present invention provides a composition comprising monophosphoryl lipid A (MPL®) or 3 De-O-acylated monophosphoryl lipid A (3D-MPL®) as an enhancer of adaptive and innate immunity. Chemically 3D-MPL® is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA), which is incorporated herein by reference. In another embodiment, the present invention provides a composition comprising synthetic lipid A, lipid A mimetics or analogs, such as BioMira's PET Lipid A, or synthetic derivatives designed to function like TLR-4 agonists.

In certain embodiments, the vaccine comprises two adjuvants. A combination of adjuvants may be selected from those described above. In one particular embodiment, the two adjuvants are MPL® and alum. In another particular embodiment, the two adjuvants are MPL® and oil.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation). Suitably effective increases in immunoglobulin levels include by more than 5%, preferably by more than 25%, and in particular by more than 50%, as compared to the same antigen composition without any adjuvant.

Delivery Agent

The invention also provides a composition comprising a delivery agent which functions to enhance antigen uptake, provide a depot effect, or increase antigen retention time at the site of delivery (e.g., delay expulsion of the antigen). Such a delivery agent may be a bioadhesive agent. In particular, the bioadhesive may be a mucoadhesive agent such as chitosan, a chitosan salt, or chitosan base (e.g., chitosan glutamate).

Chitosan, a positively charged linear polysaccharide derived from chitin in the shells of crustaceans, is a bioadhesive for epithelial cells and their overlaying mucus layer. Formulation of antigens with chitosan increases their contact time with the nasal membrane, thus increasing uptake by virtue of a depot effect (Ilium et al. 2001; 2003; Davis et al. 1999; Bacon et al. 2000; van der Lubben et al. 2001; 2001; Lim et al. 2001). Chitosan has been tested as a nasal delivery system for several vaccines, including influenza, pertussis and diphtheria, in both animal models and humans (Ilium et al. 2001; 2003; Bacon et al. 2000; Jabbal-Gill et al. 1998; Mills et al. 2003; McNeela et al. 2004). In these trials, chitosan was shown to enhance systemic immune responses to levels equivalent to parenteral vaccination. In addition, significant antigen-specific IgA levels were also measured in mucosal secretions. Thus, chitosan can greatly enhance a nasal vaccine's effectiveness. Moreover, due to its physical characteristics, chitosan is particularly well suited to intranasal vaccines formulated as powders (van der Lubben et al. 2001; Mikszta et al. 2005; Huang et al. 2004).

Accordingly, in one embodiment, the present invention provides an antigenic or vaccine composition adapted for intranasal administration, wherein the composition includes antigen and an effective amount of adjuvant. In preferred embodiments, the invention provides an antigenic or vaccine composition comprising Norovirus antigen such as Norovirus VLP, in combination with at least one delivery agent, such as chitosan, and at least one adjuvant, such as MPL®, CPG oligos, alum, oil, imiquimod, gardiquimod, or synthetic lipid A or lipid A mimetics or analogs.

The molecular weight of the chitosan may be between 10 kDa and 800 kDa, preferably between 100 kDa and 700 kDa and more preferably between 200 kDa and 600 kDa. The concentration of chitosan in the composition will typically be up to about 80% (w/w), for example, 5%, 10%, 30%, 50%, 70% or 80%. The chitosan is one which is preferably at least 75% deacetylated, for example 80-90%, more preferably 82-88% deacetylated, particular examples being 83%, 84%, 85%, 86% and 87% deacetylation.

Vaccine and Antigenic Formulations

The compositions of the invention can be formulated for administration as vaccines or antigenic formulations. As used herein, the term "vaccine" refers to a formulation which contains Norovirus VLPs or other Norovirus antigens of the present invention as described above, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs or antigen. As used herein, the term "antigenic formulation" or "antigenic composition" refers to a preparation which, when administered to a vertebrate, e.g. a mammal, will induce an immune response. As used herein, the term "immune response" refers to both the humoral immune response and the cell-mediated immune response. The humoral immune response involves the stimulation of the production of antibodies by B lymphocytes that, for example, neutralize infectious agents, block infectious agents from entering cells, block replication of said infectious agents, and/or protect host cells from infection and destruction. The cell-mediated immune response refers to an immune response that is mediated by T-Lymphocytes and/or other cells, such as macrophages, against an infectious agent, exhibited by a vertebrate (e.g., a human), that prevents or ameliorates infection or reduces at least one symptom thereof. In particular, "protective immunity" or "protective immune response" refers to immunity or eliciting an immune response against an infectious agent, which is exhibited by a vertebrate (e.g., a human), that prevents or ameliorates an infection or reduces at least one symptom thereof. Specifically, induction of a protective immune response from administration of the vaccine is evident by elimination or reduction of the presence of one or more symptoms of gastroenteritis or a reduction in the duration or severity of such symptoms. Clinical symptoms of gastroenteritis from Norovirus include nausea, diarrhea, loose stool, vomiting, fever, and general malaise. A protective immune response that reduces or eliminates disease symptoms will reduce or stop the spread of a Norovirus outbreak in a population. Vaccine preparation is generally described in Vaccine Design ("The subunit and adjuvant approach" (eds Powell M. F. & Newman M. J.) (1995) Plenum Press New York). The compositions of the present invention can be formulated, for example, for delivery to one or more of the oral, gastro-intestinal, and respiratory (e.g. nasal) mucosa. The compositions of the present invention can be formulated, for example, for delivery by injection.

Where the composition is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

Where the composition is intended for intramuscular (i.m.) injection, it is typically formulated as a liquid suspension comprised of Norovirus VLPs and an adjuvant. In one embodiment, the adjuvant may be MPL®. In another embodiment, an i.m.-formulated vaccine may have more than one adjuvant. In a preferred embodiment, an i.m.-formulated vaccine is formulated with Aluminum Hydroxide (e.g. alum) and Monophosphoryl Lipid A (MPL®). Administration of an i.m.-formulated vaccine can be by needle and syringe, as is well known in the art.

In one embodiment, the Norovirus vaccine or antigenic formulation of the present invention contains one or more Norovirus genogroup antigen(s) as the immunogen, an adjuvant such as MPL®, a biopolymer such as chitosan to promote adhesion to mucosal surfaces, and bulking agents such as mannitol and sucrose. For example, the Norovirus vaccine may be formulated as 10 mg of a dry powder containing one or more Norovirus genogroup antigen(s)

(e.g., Norwalk virus, Houston virus, Snow Mountain virus), MPL® adjuvant, chitosan mucoadhesive, and mannitol and sucrose as bulking agents and to provide proper flow characteristics. The formulation may comprise about 7.0 mg (25 to 90% w/w range) chitosan, about 1.5 mg mannitol (0 to 50% w/w range), about 1.5 mg sucrose (0 to 50% w/w range), about 25 µg MPL® (0.1 to 5% w/w range), and about 100 µg Norovirus antigen (0.05 to 5% w/w range).

Norovirus antigen may be present in a concentration of from about 0.01% (w/w) to about 80% (w/w). In one embodiment, Norovirus antigens can be formulated at dosages of about 5 µg, about 15 µg, about 25 µg, about 50 µg, about 100 µg, about 150 µg, about 200 µg, about 500 µg, and about 1 mg per 10 mg dry powder formulation (0.05, 0.15, 0.25, 0.5, 1.0, 1.5, 2.0, 5.0, and 10.0% w/w) for administration into both nostrils (10 mg per nostril) or about 10 µg, about 30 µg, about 50 µg, about 100 µg, about 200 µg, about 300 µg, about 400 µg, about 1 mg, and about 2 mgs (0.1, 0.3, 0.5, 1.0, 2.0, 3.0, 4.0, 10.0 and 20.0% w/w) per 20 mg dry powder formulation for administration into one nostril. The formulation may be given in one or both nostrils during each administration. There may be a booster administration 1 to 12 weeks after the first administration to improve the immune response. The content of each Norovirus antigen in the vaccine and antigenic formulations may be in the range of 1 µg to 100 mg, preferably in the range 1-1000 µg, more preferably 5-500 µg, most typically in the range 10-200 µg. Total Norovirus antigen administered at each dose can be either about 10 µg, about 25 µg, about 30 µg, about 50 µg, about 60 µg, about 70 µg, about 80 µg, about 90 µg, about 100 µg, about 125 µg, about 150 µg, about 175 µg, about 200 µg, about 250 µg, about 300 µg, about 400 µg, about 500 µg, or about 1000 µg. The total vaccine dose can be administered into one nostril or can be split in half for administration to both nostrils. Dry powder characteristics are such that less than 10% of the particles are less than 10 µm in diameter. Mean particle sizes range from 10 to 500 µm in diameter.

In another embodiment, the antigenic and vaccine compositions can be formulated as a liquid for subsequent administration to a subject. A liquid formulation intended for intranasal administration would comprise Norovirus genogroup antigen(s), adjuvant, and a delivery agent such as chitosan. Liquid formulations for intramuscular (i.m.) administration would comprise Norovirus genogroup antigen(s), adjuvant, and a buffer, without a delivery agent (e.g., chitosan). In one embodiment, a liquid formulation for i.m. administration comprises Norovirus genogroup antigen(s), MPL®, alum, and a buffer. In another embodiment, a liquid formulation for i.m. administration comprises Norovirus genogroup antigen(s), MPL®, oil, and a buffer.

Preferably the antigenic and vaccine compositions hereinbefore described are lyophilized and stored anhydrous until they are ready to be used, at which point they are reconstituted with diluent. Alternatively, different components of the composition may be stored separately in a kit (any or all components being lyophilized). The components may remain in lyophilized form for dry formulation or be reconstituted for liquid formulations, and either mixed prior to use or administered separately to the patient. For dry powder administration, the vaccine or antigenic formulation may be preloaded into an intranasal delivery device and stored until use. Preferably, such intranasal delivery device would protect and ensure the stability of its contents.

The lyophilization of antigenic formulations and vaccines is well known in the art. Typically the liquid antigen is freeze dried in the presence of agents to protect the antigen during the lyophilization process and to yield a cake with desirable powder characteristics. Sugars such as sucrose, mannitol, trehalose, or lactose (present at an initial concentration of 10-200 mg/mL) are commonly used for cryoprotection of protein antigens and to yield lyophilized cake with desirable powder characteristics. Lyophilizing the compositions theoretically results in a more stable composition. While the goal of most formulation processes is to minimize protein aggregation and degradation, the inventors have discovered that the presence of aggregated antigen enhances the immune response to Norovirus VLPs (see Examples 3 and 4). Therefore, the inventors have developed methods by which the percentage of aggregation of the antigen can be controlled during the lyophilization process to produce an optimal ratio of aggregated antigen to intact antigen to induce a maximal immune response.

Thus, the invention also encompasses a method of making Norovirus antigen formulations comprising (a) preparing a pre-lyophilization solution comprising Norovirus antigen, sucrose, and chitosan, wherein the ratios of sucrose to chitosan are from about 0:1 to about 10:1; (b) freezing the solution with liquid nitrogen; and (c) lyophilizing the frozen solution at ambient temperature for 48-72 hours, wherein the final lyophilized product contains a percentage of said Norovirus antigen in aggregated form. In one embodiment, the pre-lyophilization solution further comprises a bulking agent. In another embodiment, said bulking agent is mannitol.

Appropriate ratios of sucrose and chitosan to yield desired percentages of aggregation can be determined by the following guidelines. A pre-lyophilization mixture containing a weight ratio of sucrose to chitosan in a range from about 2.5:1 to about 10:1 will yield greater than 95% intact Norovirus antigen post-lyophilization (i.e. less than 5% aggregated antigen). A range of sucrose to chitosan weight ratios of about 1:1 to about 2.1:1 will yield about 50% to about 90% intact Norovirus antigen (i.e. about 10% to about 50% aggregated antigen). Weight ratios of 0:1 sucrose to chitosan will produce less than 30% of intact Norovirus antigen. Omission of both sucrose and chitosan will produce less than 5% intact antigen (i.e. greater than 95% aggregated antigen). Using these guidelines, the skilled artisan could adjust the sucrose to chitosan weight ratios in the pre-lyophilization mixture to obtain the desired amount of aggregation necessary to produce an optimal immune response.

In addition, the inclusion of sucrose and chitosan to the pre-lyophilization solution promotes the stability of the intact Norovirus antigen over time. The ratio of aggregated antigen/intact antigen in the formulation does not increase when stored as a dry powder for a period of about 12 months or greater. Thus, this lyophilization procedure ensures stable formulations with predictable and controllable ratios of aggregated to intact Norovirus antigen.

Methods of Stimulating an Immune Response

The amount of antigen in each antigenic or vaccine formulation dose is selected as an amount which induces a robust immune response without significant, adverse side effects. Such amount will vary depending upon which specific antigen(s) is employed, route of administration, and adjuvants used. In general, the dose administered to a patient, in the context of the present invention should be sufficient to effect a protective immune response in the patient over time, or to induce the production of antigen-specific antibodies. Thus, the composition is administered to a patient in an amount sufficient to elicit an immune response to the specific antigens and/or to prevent, alleviate, reduce, or cure symptoms and/or complications from the disease or infection, and thus reduce or stop the spread of a Norovirus outbreak in a population. An amount adequate to accomplish this is defined as a "therapeutically effective dose."

For a substantially pure form of the Norovirus antigen, it is expected that each dose will comprise about 1 µg to 10 mg, preferably about 15-500 µg for each Norovirus antigen in the formulation. In a typical immunization regime employing the antigenic preparations of the present invention, the formulations may be administered in several doses (e.g. 1-4), each dose containing 1-1000 µg of each antigen. Total Norovirus antigen administered at each dose can be either about 10 µg, about 25 n, about 30 about 50 µg, about 60 about 70 µg, about 80 µg, about 90 µg, about 100 µg, about 125 µg, about 150 µg, about 175 µg, about 200 µg, about 250 µg, about 300 µg, about 400 µg, about 500 µg, or about 1000 µg. The dose will be determined by the immunological activity the composition produced and the condition of the patient, as well as the body weight or surface areas of the patient to be treated. The size of the dose also will be determined by the existence, nature, and extent of any adverse side effects that may accompany the administration of a particular composition in a particular patient.

The antigenic and vaccine formulations of the present invention may be administered via a non-mucosal or mucosal route. These administrations may include in vivo administration via parenteral injection (e.g. intravenous, subcutaneous, and intramuscular) or other traditional direct routes, such as buccal/sublingual, rectal, oral, nasal, topical (such as transdermal and ophthalmic), vaginal, pulmonary, intraarterial, intraperitoneal, intraocular, or intranasal routes or directly into a specific tissue. Alternatively, the vaccines of the invention may be administered by any of a variety of routes such as oral, topical, subcutaneous, mucosal, intravenous, intramuscular, intranasal, sublingual, transcutaneous, subdermal, intradermal and via suppository. In one embodiment, the vaccine is administered by an intramuscular route of administration. Administration may be accomplished simply by direct administration using a needle, catheter or related device, at a single time point or at multiple time points.

In a preferred embodiment, the antigenic and vaccine formulations of the present invention are administered by the intranasal route. Immunization via the mucosal surfaces offers numerous potential advantages over other routes of immunization. The most obvious benefits are 1) mucosal immunization does not require needles or highly-trained personnel for administration, and 2) immune responses are raised at the site(s) of pathogen entry, as well as systemically (Isaka et al. 1999; Kozlowski et al. 1997; Mestecky et al. 1997; Wu et al. 1997).

In a further aspect, the invention provides a method of eliciting an IgA mucosal immune response and an IgG systemic immune response by administering (preferably intranasally) to a mucosal surface of the patient an antigenic or vaccine composition comprising one or more Norovirus antigens, at least one effective adjuvant and/or at least one delivery agent. In one embodiment, the immune response is a highly-biased mucosal response, i.e. characterized by a large increase in serum IgA relative to serum IgG. For instance, in some embodiments, the immune response is characterized by a ratio of serum IgA mean fold rise titer to serum IgG mean fold rise titer of from about 1.5:1 to about 3:1.

In a further aspect, the invention provides a method of boosting a pre-existing mucosal immune response by administering the vaccine of the invention parenterally, including but not limited to the intramuscular route.

The present invention also contemplates the provision of means for dispensing formulations of Norovirus antigens hereinbefore defined, and at least one adjuvant or at least one delivery agent as hereinbefore defined. A dispensing device for intranasal formulations may, for example, take the form of an aerosol delivery system, and may be arranged to dispense only a single dose, or a multiplicity of doses. Such a device would deliver a metered dose of the vaccine or antigenic formulation to the nasal passage. Other examples of appropriate devices include, but are not limited to, droppers, swabs, aerosolizers, insufflators (e.g. Valois Monopowder Nasal Administration Device, single dose Bespak UniDose DP dry powder intranasal delivery device), nebulizers, and inhalers. The devices may deliver the antigenic or vaccine formulation by passive means requiring the subject to inhale the formulation into the nasal cavity. Alternatively, the device may actively deliver the formulation by pumping or spraying a dose into the nasal cavity. The antigenic formulation or vaccine may be delivered into one or both nostrils by one or more such devices. Administration could include two devices per subject (one device per nostril). In a preferred embodiment, the antigenic or vaccine formulation is administered to the nasal mucosa by rapid deposition within the nasal passage from a device containing the formulation held close to the nasal passageway. For intraparenteral formulations (e.g. intramuscular formulations), a dispensing device can be a syringe equipped with a needle or an autoinjector.

Actual dose of active ingredient (Norovirus antigen) may be about 5-1000 µg. In certain embodiments, the actual dose of Norovirus antigen per device is about 50 µg or about 100 µg. In certain embodiments, the actual dose of Norovirus antigen per device is about 150 µg or about 300 µg. In other embodiments, the actual dose of Norovirus antigen per device is about 300 µg or about 600 µg.

The invention also provides a method of generating antibodies to one or more Norovirus antigens, said method comprising administration of a vaccine or antigenic formulation of the invention as described above to a subject. These antibodies can be isolated and purified by routine methods in the art. The isolated antibodies specific for Norovirus antigens can be used in the development of diagnostic immunological assays. These assays could be employed to detect a Norovirus in clinical samples and identify the particular virus causing the infection (e.g. Norwalk, Houston, Snow Mountain, etc.). Alternatively, the isolated antibodies can be administered to subjects susceptible to Norovirus infection to confer passive or short-term immunity.

The invention provides methods for eliciting protective immunity to a Norovirus infection in a subject comprising administering a vaccine to the subject, wherein said vaccine comprises Norovirus VLPs and at least one adjuvant. In one embodiment, the subject is a human and the vaccine confers protection from one or more symptoms of Norovirus infection. Although others have reported methods of inducing an immune response with Norovirus antigens (see U.S. Patent Application Publication No. US 2007/0207526), no one has demonstrated the induction of a protective immune response in humans. Unlike several vaccines currently licensed in the U.S. where effectiveness of the vaccine correlates with serum antibodies, studies have shown that markers of an immune response, such as increased titers of serum antibodies against Norwalk virus, are not associated with protective immunity in humans (Johnson et al. (1990) J. Infectious Diseases 161: 18-21). Moreover, another study examining Norwalk viral challenge in humans indicated that susceptibility to Norwalk infection was multifactorial and included factors such as secretor status and memory mucosal immune response (Lindesmith et al. (2003) Nature Medicine 9: 548-553). Because Norovirus is not able to be cultured in vitro, no viral neutralization assays are currently available. A functional assay which serves as a substitute for the neutralization assay is the hemagglutination inhibition (HAI) assay. HAI measures the ability of Norovirus vaccine-induced antibodies to inhibit the agglutination of antigen-coated red blood cells by Norovirus VLPs because Norovirus VLPs bind to red blood cell antigens. This assay is also known as a carbohydrate blocking assay, as it is indicative of the functional ability of antibodies to block binding of the virus or VLPs to blood group antigen carbohydrates on a red blood cell. In this assay, a fixed amount of Norovirus VLPs is mixed with a fixed amount of red blood cells and serum from immunized subjects. If the serum sample contains functional antibodies, the antibodies will compete with the VLPs for binding to the red blood cells, thereby inhibiting the agglutination of the red blood cells. As used herein, "functional antibodies" refer to antibodies that are capable of inhibiting the interaction between Norovirus particles and red blood cell antigens. The serum titer of Norovirus-specific functional antibodies can be measured by the HAI assay described above. An increase in the level of Norovirus-specific functional antibodies can be an indicator of a protective immune response. Thus, in one embodiment, the administration of the vaccine elicits a protective immunity comprising an increase in the serum titer of Norovirus-specific functional antibodies as compared to the serum titer in a human not receiving the vaccine. The serum titer of Norovirus-specific functional antibodies indicative of a protective immune response is preferably a geometric mean titer greater than 40, 50, 75, 100, 125, 150, 175, or 200 titer/mL as measured by the HAI assay. In one embodiment, the serum titer of Norovirus-specific functional antibodies is a geometric mean titer greater than 40 titer/mL as measured by the HAI assay. In another embodiment, the serum titer of Norovirus-specific functional antibodies is a geometric mean titer greater than 100 titer/mL as measured by the HAI assay.

In certain embodiments, the administration of the vaccine elicits a protective immunity comprising an increase in the level of IgA Norovirus-specific antibody secreting cells in the blood as compared to the level in a human not receiving the vaccine. In some embodiments, the administration of the vaccine elicits a protective immunity comprising an increase in the level of IgA Norovirus-specific antibody secreting cells in the blood as compared to the level in the human before receiving the vaccine. In one embodiment, the IgA Norovirus-specific antibody secreting cells are CD19+, CD27+, CD62L+, and α4β7+. Antibody secreting cells with this marker profile are capable of homing to both peripheral lymphoid tissue, such as Peyer's patch in the gut, and mucosal lymphoid tissue, such as the gut mucosa. The inventors have surprisingly discovered that the Norovirus vaccines of the invention induce this dual homing population (to both peripheral and mucosal lymphoid tissues) of IgA-secreting antibody secreting cells when administered intranasally in humans. This result is particularly surprising because intranasal vaccines do not typically induce protection in the gut. In one embodiment, the number of CD19+, CD27+, CD62L+, and α4β7+ IgA antibody secreting cells is greater than about 500, about 700, about 1,000, about 1,500, or greater than about 2,000 cells per $1\times10^6$ peripheral blood monocytes. In another embodiment, the IgA Norovirus-specific antibody secreting cells are CD19+, CD27+, CD62L-, and α4β7+. Antibody secreting cells with this marker profile generally exhibit homing only to mucosal sites and can be indicative of a memory B-cell response. In some embodiments, the number of CD19+, CD27+, CD62L-, and α4β7+ IgA antibody secreting cells is greater than about 2,000, about 2,500, about 3,000, about 4,500, about 5,000, or greater than about 6,500 cells per $1\times10^6$ peripheral blood monocytes.

Similar findings have been observed with vaccines for other viruses, such as rotavirus. For rotavirus vaccines, there is controversy over whether serum antibodies are directly involved in protection or merely reflect recent infection (Jiang, 2002; Franco, 2006). Defining such correlates of protection is particularly difficult in the context of diarrheal diseases such as rotavirus or norovirus, where preclinical studies inferring protection may be multifaceted with contributions from mucosal immunity (such as intestinal IgA), cytokine elaboration, and cell mediated immunity. The difficulty in measuring such immune responses during clinical development, and the lack of correlation to serum antibody measurements, requires that the effectiveness of a vaccine for these types of viruses can only be demonstrated through human clinical challenge experiments.

As mentioned above, administration of the vaccine of the present invention prevents and/or reduces at least one symptom of Norovirus infection. Symptoms of Norovirus infection are well known in the art and include nausea, vomiting, diarrhea, and stomach cramping. Additionally, a patient with a Norovirus infection may have a low-grade fever, headache, chills, muscle aches, and fatigue. The invention also encompasses a method of inducing a protective immune response in a subject experiencing a Norovirus infection by administering to the subject a vaccine formulation of the invention such that at least one symptom associated with the Norovirus infection is alleviated and/or reduced. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of a Norovirus infection or additional symptoms, a reduced severity of Norovirus symptoms or suitable assays (e.g. antibody titer, RT-PCR antigen detection, and/or B-cell or T-cell activation assay). An effective response may also be determined by directly measuring (e.g., RT-PCR) virus load in stool samples, which reflects the amount of virus shed from the intestines). The objective assessment comprises both animal and human assessments.

Stability and efficacy in animal models of the vaccine and antigenic formulations disclosed herein are reported in International Application No. PCT/US07/79929, which is herein incorporated by reference in its entirety.

EXAMPLES

The invention will now be illustrated in greater detail by reference to the specific embodiments described in the following examples. The examples are intended to be purely illustrative of the invention and are not intended to limit its scope in any way.

Example 1

GLP Toxicity Study of Norovirus Vaccine Formulations in Rabbits

The purpose of this study was to evaluate the potential toxicity of a Norwalk virus-virus-like particle (NV-VLP)

vaccine following three intranasal doses in rabbits. The NV-VLP vaccine contained (per 10 mg dry powder) 25 µg of a Genogroup I VLP, 25 µg MPL, 7 mg chitosan glutamate, 1.475 mg mannitol, and 1.475 mg sucrose. The study was conducted over an eight week period. The persistence, reversibility, or delayed onset of any effects were assessed after a four-week, no-treatment recovery interval. Sixty New Zealand White rabbits (30/sex) were randomly assigned to three groups (10 rabbits/sex/group). Group 1 animals were not dosed (i.e. naïve). Group 2 animals were administered 10 mg/nostril (20 mg total) of placebo (i.e. adjuvant/excipient: MPL, chitosan, sucrose, and mannitol). Group 3 animals were administered 10 mg/nostril (20 mg total) of NV-VLP vaccine, which represented 25 µg of antigen per nostril (50 µg total). Animals in groups 2 and 3 were dosed on study day (SD) 1, 22, and 43 by intranasal administration using the Bespak Unidose intranasal dry powder device. Animals (5/group/sex) were subjected to a full gross necropsy on SD 46 and 74. Parameters evaluated during the study included mortality, clinical and cageside observations, body weights, body weight changes, food consumption, body temperature, ophthalmology examinations, clinical pathology (clinical chemistry, hematology, and urinalysis), gross pathology, organ weight data, and histopathology. The study outline is summarized in Table 1. The conclusions of the study are summarized in Table 2.

TABLE 1

Study Parameters for GLP Toxicity Study of Norwalk Vaccine Formulation

| | |
|---|---|
| Species | SPF New Zealand White Rabbits with ear tag IDs |
| No. Animals/Sex/Dose Group | 10 males and 10 females/group |
| Total Number of Animals in Study | 60 |
| Group 1 | Non-treated controls |
| Group 2 | Adjuvant/Excipient |
| Group 3 | 1x maximum human dose VLPs in Adjuvant/Excipient |

TABLE 2

Safety and Toxicology Findings for Norwalk Vaccine Formulation

| | |
|---|---|
| Observations | No treatment related effects on mortality, clinical or cageside observations. |
| Body weight and body weight changes | No adverse effect on body weights or body weight changes. |
| Food consumption | No treatment related adverse effect on food consumption. |
| Body temperature | No treatment related adverse effect on body temperature. |
| Opthamology | No ocular lesions were noted in any animal over the course of the study. |
| Clinical Pathology | Polyclonal activation of B lymphocyte populations in rabbits receiving NV-VLP Vaccine or Adjuvant/Excipient was noted days 3-76. Absolute monocyte values were elevated in rabbits receiving NV-VLP Vaccine or Adjuvant/Excipient on days 3-46. There were no treatment effects on selected urinalysis parameters. |
| Gross Pathology | No treatment related observations. |
| Organ weights | No adverse effects on absolute or relative organ weights. |
| Histopathology | Varying degrees of inflammatory infiltrates, either within the lamina propria of nasal turbinates or free within the nasal passages, and/or hemorrhage within the nasal passages of rabbits receiving NV-VLP Vaccine or Adjuvant/Excipient. The observed lesions are those that would be expected in an immunologic reaction. Lesions in both groups were limited in nature and resolved completely by SD 74. |

Cage side observations revealed no significant findings. Hematological measures (increases in globulin and total protein) were typical of B lymphocyte polyclonal activation and may be attributable to adjuvant effects. Histopathology findings consisted of varying degrees of inflammatory infiltrates, either within the lamina propria of nasal turbinates or free within the nasal passages, and/or mild hemorrhage in the nasal passages of rabbits in both groups. The observed lesions would be expected in an immunologic reaction. Lesions in both groups were limited in nature and resolved completely by study day 74.

Serological samples analyzed by ELISA for NV-VLP specific IgG showed measurable anti-NV-VLP titers in 30% of the immunized animals on day 10 following a single dose (see FIG. 1). Boost treatments on days 22 and 43 increased both the number of seroconverted animals and levels of product-specific antibodies, and by day 73, 90% of the immunized animals seroconverted. None of the naïve or matrix treated controls had quantifiable levels of NV-VLP specific antibodies (data not shown).

The immune response was further characterized by evaluating memory B-cell responses in an additional set of rabbits immunized intranasally with the same formulation on days 1, 15 and 29. Memory B-cell responses were measured as described in International Application No. PCT/US07/79929, which is herein incorporated by reference in its entirety. Tissues collected 156 days after the last boost showed the presence of NV-VLP-specific memory B-cells in the peripheral blood, the spleen, and most notably, in the mesenteric lymph nodes. The antigen-specific memory B-cells in the mesenteric lymph nodes were IgA positive. Additionally, NV-VLP-specific antibody-secreting long-lived plasma cells were present in the bone marrow.

Example 2

Dose Escalation Safety Study of Norwalk Vaccine Formulation in Humans (LV01-101 Study)

A double-blind, controlled, dose-escalation phase 1 study of the safety and immunogenicity of a Norovirus genogroup 1 vaccine was conducted. The vaccine consisted of lyophilized Norwalk virus-like particles (VLPs) in a dry powder matrix designed for intranasal administration. Vaccinees included healthy adult volunteers who were H type 1 antigen secretors. The rationale for enrollment of H type 1 antigen secretors is that H type 1 antigen secretors are susceptible to Norwalk viral infections while non-secretors are resistant. Saliva was collected from volunteers to determine H type 1 antigen secretor status. As a control, 2 additional volunteers at each dosage level received matrix alone. The dry powder matrix included 25 µg MPL® adjuvant, 7 mg chitosan, 1.5 mg mannitol, and 1.5 mg sucrose. Volunteers were dosed on days 0 and 21 and were required to keep a 7-day diary of symptoms after each dose. Blood for serology, antibody secreting cells (ASC), and stool and saliva samples for mucosal antibody evaluation were collected.

The components of the Norwalk VLP vaccine are listed in Table 3. The vaccine is packaged in an intranasal delivery device. Single administrations of Norwalk VLP Vaccine were packaged in a single dose Bespak (Milton Keynes, UK) UniDose DP dry powder intranasal delivery device. Each device delivered 10 mg of the dry powder vaccine formulation. Each dose of vaccine consisted of two delivery devices, one in each nostril. The total vaccine dose was 20 mg of dry power. The formulation of Adjuvant/Excipient is the same as the Norwalk VLP Vaccine except that no Norwalk VLP antigen is included in the formulation. The formulation of the Adjuvant/Excipient (also referred to as dry powder matrix) is summarized in Table 4.

TABLE 3

Norwalk VLP Vaccine Composition

| Component | Molecular class | Quantity per 10 mg dry powder | % of Final Formulation |
|---|---|---|---|
| Norwalk VLP | Recombinant protein | 2.5, 7.5, 25, or 50 µg | 0.025, 0.075, 0.25, or 0.50% |
| Monophosphoryl Lipid A | Phospholipid | 25 µg | 0.25% |
| Chitosan | Polysaccharide | 7.0 mg | 70% |
| Mannitol | Sugar | 1.5 mg | 15%* |
| Sucrose | Sugar | 1.5 mg | 15% |

*Quantity of mannitol varies slightly in different formulations to account for variation in Norwalk VLP content.

TABLE 4

Adjuvant/Excipient (dry powder matrix)

| Component | Molecular class | Quantity per 10 mg dry powder | % of Final Formulation |
|---|---|---|---|
| Monophosphoryl Lipid A | Phospholipid | 25 µg | 0.25% |
| Chitosan | Polysaccharide | 7.0 mg | 70% |
| Mannitol | Sugar | 1.5 mg | 15% |
| Sucrose | Sugar | 1.5 mg | 15% |

Specifically, the dose escalation of the vaccine was conducted as follows: After appropriate screening for good health, a group of 3 volunteers was randomized to receive either 5 µg Norwalk VLP Vaccine plus dry powder matrix (n=2) or dry powder matrix alone (n=1) by the intranasal route. These 3 volunteers were followed for safety for 21 days and their safety data reviewed by the Independent Safety Monitor (ISM). Upon approval of the ISM, these individuals received their second dose of Vaccine or matrix on day 21, and 4 additional volunteers were randomized to receive either 5 µg VLP protein plus dry powder matrix (n=3) or matrix alone (n=1) by the intranasal route. The ISM reviewed the safety data from this second group and upon approval of the ISM, the second intranasal dose was given 21 days after the first dose. Volunteers kept a 7-day diary of symptoms after each dose. After the ISM determined that escalation to the next higher dose was acceptable, another group of 7 volunteers was randomized to receive either Norwalk VLP Vaccine containing 15 µg VLP protein (n=5) or dry powder matrix alone (n=2) by the intranasal route at day 0 and day 21. Again, 7-day symptom diaries were recorded and reviewed by the ISM before the second dose at day 21. Finally, after review of the safety data from the first two dosage cohorts, the ISM determined that dose escalation was acceptable and a final group of 7 volunteers were randomized to receive either Norwalk VLP Vaccine containing 50 µg VLP protein (n=5) or dry powder matrix alone (n=2) by the intranasal route on day 0 and day 21. Seven-day symptom diaries and other safety data were again reviewed by the ISM before the second dose at day 21.

The volunteers kept a daily diary of symptoms (including local symptoms such as: nasal discharge, nasal pain/discomfort, nasal congestion, runny nose, nasal itching, nose bleed, headache and systemic symptoms such as: daily oral temperature, myalgia, nausea, vomiting, abdominal cramps, diarrhea, and loss of appetite) for 7 days after receiving Norwalk VLP Vaccine or dry powder matrix alone. Interim medical histories were obtained at each follow-up visit (days 7±1, 21±2, 28±2, 56±2 and 180±14); volunteers were queried about interim illness, medications, and doctor's visits. Volunteers were asked to report all serious or severe adverse events including events that were not solicited during follow up visits. Volunteers had CBC and serum creatinine, glucose, AST, and ALT assessed on days 7 and 28 (7 days after each immunization) and, if abnormal, the abnormal laboratory test was followed until the test became normal or stabilized.

The blinded data indicated that of the volunteers that received the low dose (n=5) or matrix (n=2), 4 of 7 reported some or all of the following: nasal discharge, nasal pain, stuffiness, itching, sneezing, headache, and/or sore throat in the first 24 hours after vaccination. One volunteer reported a minor nosebleed on each of days 1 and 6. Of the volunteers that received the middle dose (n=5) or matrix (n=2), 5 of 7 reported mild nasal discharge, stuffiness, itching, sneezing, and/or headache in the first 24 hours. Symptoms generally resolved in the first 72 hours, but stuffiness persisted to day 7 in one volunteer. A summary of the findings on the unblinded data is presented in Table 5 below, which also includes adverse events reported in the high dose. These findings indicate that intranasal Norovirus VLP vaccine is associated with local, usually mild, short-lived symptoms that appeared to be independent of VLP concentration. No differences were seen between the adjuvant/excipient (or matrix) control group and the Norwalk VLP vaccine groups for adverse events, hematology, blood chemistry and/or physical examination results.

TABLE 5

Number of Volunteers with Adverse Events to Norwalk VLP Vaccine or Adjuvant/Excipient

| Reported Adverse Events | Adjuvant/ Excipient (N = 6) | Low Dose (N = 5) | Mid Dose (N = 5) | High Dose (N = 5)* |
|---|---|---|---|---|
| Nose and Throat | | | | |
| Nasal Stuffiness | 4 | 2 | 3 | 1 |
| Nasal Itching | 3 | 3 | 2 | 2 |
| Nasal Discharge | 3 | 3 | 4 | 3 |

TABLE 5-continued

Number of Volunteers with Adverse Events to Norwalk VLP Vaccine or Adjuvant/Excipient

| Reported Adverse Events | Adjuvant/ Excipient (N = 6) | Low Dose (N = 5) | Mid Dose (N = 5) | High Dose (N = 5)* |
|---|---|---|---|---|
| Nasal Pain | — | 2 | 1 | 2 |
| Sneezing | 3 | 2 | 1 | 3 |
| Nose Bleed | — | 1 | 1 | — |
| Sore Throat/URI | — | 1 | — | 1 |
| Itchy Sore Throat | — | 1 | — | — |
| Burning in Nose/Throat | — | 1 | — | 1 |
| Chest | | | | |
| Cough | 2 | — | — | — |
| Chest discomfort | — | — | — | 1 |
| Systemic | | | | |
| Headache | 2 | 2 | 1 | 1 |
| Malaise | 3 | 2 | — | 1 |
| Nausea | — | 1 | — | 1 |
| Abdominal Cramp | 1 | — | — | 1 |
| Laboratory | | | | |
| ALT/AST | — | 1 | — | — |
| AST | 1 | — | — | — |
| ALT | — | — | — | 1 |
| Alk Phos | — | — | — | 1 |
| Gastrointestinal | | | | |
| Diarrhea | — | 1 | — | 1 |
| Loss of appetite | 1 | — | 1 | — |
| No Adverse Events Reported | | | | |
|  | — | — | 1 | 2 |

*One subject in cohort 3 did not receive the second dose

Blood was collected before immunization and on days 7±1, 21±2, 28±2, 56±2, and 180±14 to measure serum antibodies to Norwalk VLP Vaccine by enzyme-linked immunosorbent assays (ELISA). Before and on day 7 after administration of each dose of Vaccine or dry powder matrix alone peripheral blood lymphocytes were collected to detect antibody secreting cells by ELISPOT assay. Before and on days 21±2, 56±2 and 180±14 after vaccination, whole blood was obtained to separate cells and freeze for future studies of cell mediated immunity, including cytokine production in response to Norwalk VLP antigen, and lymphoproliferation. Finally blood from volunteers receiving the highest dose of Norwalk VLPs (50 third cohort described above) was screened for memory B-cells on days 0, 21, 56 and 180.

The following methods were used to analyze the blood samples collected from immunized individuals or individuals receiving the dry powder matrix alone:

A. Serum Antibody Measurements by ELISA

Figure 2:
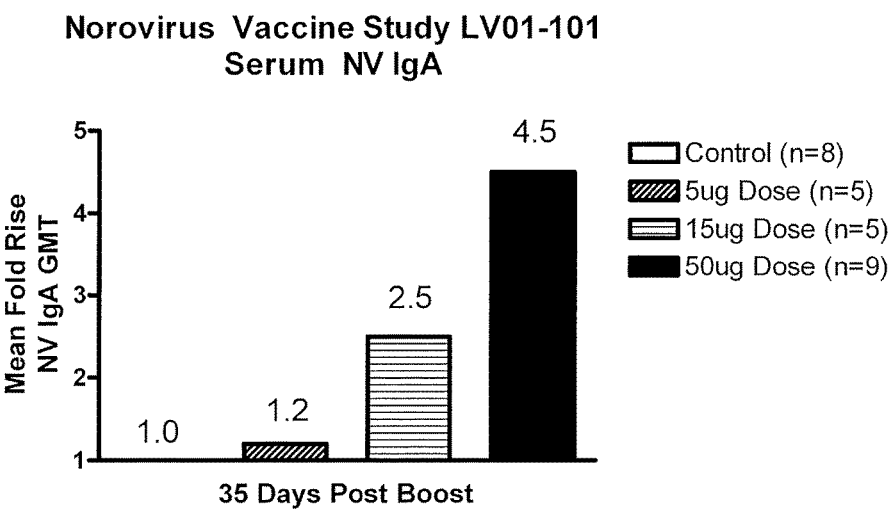
FIG. 2 depicts the results of ELISA assays measuring serum IgA (panel A) and IgG (panel B) levels from human volunteers immunized with control (adjuvant/excipient) or a vaccine formulation containing one of three doses of Norwalk Virus VLPs (5, 15, or 50 μg). The geometric mean fold-increase in anti-VLP titer is shown for each of the dosage levels at 35 days after the second immunization (day 56). Volunteers received immunizations on days 0 and 21.
Figure 2:
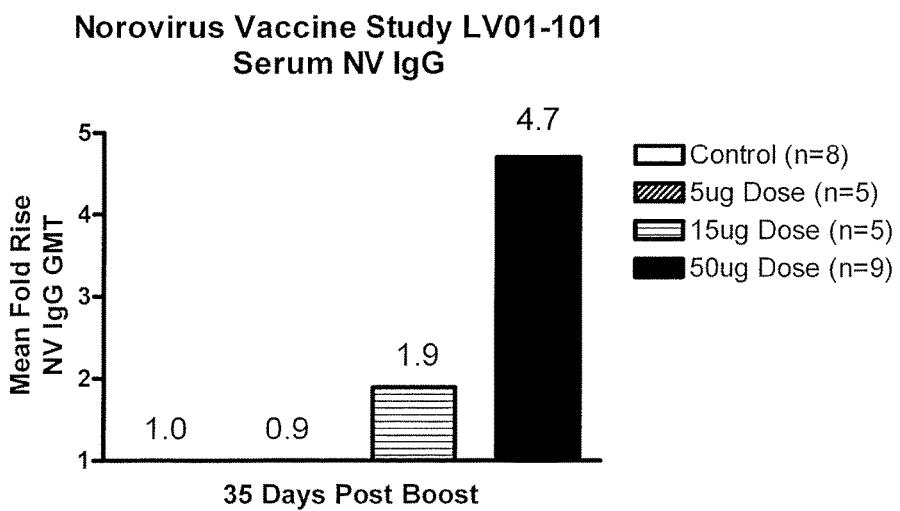

Twenty mL of blood were collected before and at multiple time points after vaccination for measurement of antibodies to Norwalk virus by ELISA, using purified recombinant Norwalk VLPs as target antigen to screen the coded specimens. Briefly, Norwalk VLPs in carbonate coating buffer pH 9.6 were used to coat microtiter plates. Coated plates were washed, blocked, and incubated with serial two-fold dilutions of test serum followed by washing and incubation with enzyme-conjugated secondary antibody reagents specific for human IgG, IgM, and IgA. Appropriate substrate solutions were added, color developed, plates read, and the IgG, IgM, and IgA endpoint titers were determined in comparison to a reference standard curve for each antibody class. A positive response was defined as a 4-fold rise in titer after vaccination. The geometric mean serum titers for IgG and IgA are shown at day 0, 7, 21, 28, 56, and 180 for each vaccine dose in FIGS. 4A and B, respectively. The mean fold rise in geometric mean titer at day 56 (35 days after the second immunization) for each of the vaccine doses is shown in FIG. 2. The results show a dose-dependent increase in serum titers for IgG and IgA. A significant serum titer for both IgG and IgA was observed in volunteers receiving the vaccine containing 50 μg of Norovirus antigen.

B. Antibody Secreting Cell Assays

PBMCs were collected from heparinized blood (30 mL for cohorts 1 and 2, 25 mL for cohort 3) for ASC assays to detect cells secreting antibodies to Norwalk VLPs. These assays were performed on days 0, 7±1, 21±2, and 28±2 after administration of Norwalk VLP Vaccine or dry powder matrix alone. The response rate and mean number of ASC per $10^6$ PBMC at each time point for each dosage were described. A positive response was defined as a post-vaccination ASC count per $10^6$ PBMCs that is at least 3 standard deviations (SD) above the mean pre-vaccination count for all subjects (in the log metric) and at least 8 ASC spots, which corresponds to the mean of medium-stimulated negative control wells (2 spots) plus 3 SD as determined in similar assays.

Figure 3:
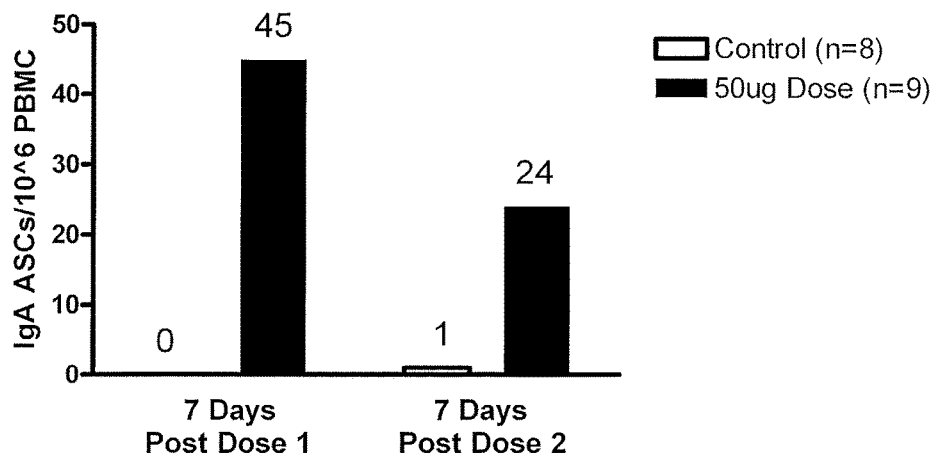
FIG. 3 shows the levels of IgA (panel A) and IgG (panel B) antibody secreting cells (ASCs) in human volunteers receiving vaccine formulations with the 50 μg dose of Norwalk Virus VLPs or control (adjuvant/excipient). The geometric mean (GMN) of ASCs per $10^6$ peripheral blood mononuclear cells (PBMCs) is plotted versus study day (day 7 or day 28), specifically seven days post immunization. Volunteers received immunizations on days 0 and 21.
Figure 3:
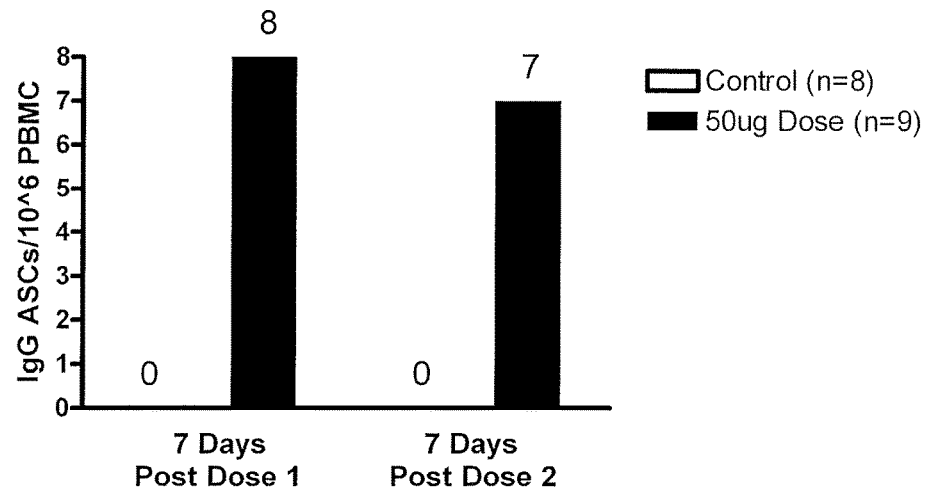

The results of the ASC assays for the 50 μg dose of Norwalk VLPs are depicted in FIG. 3. Circulating IgG and IgA antibody secreting cells were observed seven days after initial and boost vaccinations, suggesting that the vaccine is immunogenic.

C. Measurement of Functional Antibody Response

Serum collected as described in paragraph B, above, was further analyzed to determine the functional properties of the anti-Norwalk virus antibodies. Serial two-fold dilutions of test serum were analyzed with respect to their ability to inhibit hemagglutination of red blood cells by Norwalk VLPs (a functional assay to indicate protective immune responses). A positive response was defined as a 4-fold rise in titer after vaccination. The serum titers and hemagglutination inhibition titers at day 56 (35 days post boost) for five subjects who received the 50 μg dose of the Norwalk VLPs vaccine are shown in Table 6. The results show that seventy five percent (75%) of the individuals who exhibited a seroconversion response as measured by serum IgG titers also developed a functional antibody response capable of blocking the binding receptor on human red blood cells as measured by hemagglutination inhibition.

TABLE 6

Serum IgG and Hemagglutination Inhibition (HAI) (functional) Titers on Day 0 and Day 35 Post Boost (35PB) for Five Human Volunteers.

| Subject Reference | Day 0 | Day 35PB |
|---|---|---|
| Serum IgG Titers | | |
| A | 2,444.6 | 37,185.9 |
| B | 4,462.1 | 23,508.4 |
| C | 7,735.7 | 13,357.8 |
| D | 884.5 | 4,577.5 |
| E | 12,719.0 | 91,710.8 |
| Hemagglutination Inhibition (HAI) Titers | | |
| A | 8 | 256 |
| B | 8 | 256 |
| C | 512 | 512 |
| D | <8 | 8 |
| E | 128 | 1024 |

D. Measurement of Norwalk Virus-Specific Memory B-Cells

Heparinized blood was collected from cohort 3 (30 mL days 0 and 21, 50 mL days 56 and 180) to measure memory B cells on days 0, 21, 56 and 180 after vaccination using an ELISpot assay preceded by an in vitro antigen stimulation. A similar assay was successfully used to measure frequency of memory B cells elicited by Norwalk VLP formulations in rabbits (See International Application No. PCT/US07/79929, herein incorporated by reference). Peripheral blood mononuclear cells ($5 \times 10^6$ cells/mL, 1 mL/well in 24-well plates) are incubated for 4 days with Norwalk VLP antigen (2-10 µg/mL) to allow for clonal expansion of antigen-specific memory B cells and differentiation into antibody secreting cells. Controls include cells incubated in the same conditions in the absence of antigen and/or cells incubated with an unrelated antigen. Following stimulation, cells are washed, counted and transferred to ELISpot plates coated with Norwalk virus VLP. To determine frequency of virus-specific memory B cells per total Ig-secreting B lymphocytes, expanded B cells are also added to wells coated with anti-human IgG and anti-human IgA antibodies. Bound antibodies are revealed with HRP-labeled anti-human IgG or anti-human IgA followed by True Blue substrate. Conjugates to IgA and IgG subclasses (IgA1, IgA2 and IgG1-4) may also be used to determine antigen-specific subclass responses which may be related with distinct effector mechanisms and locations of immune priming. Spots are counted with an ELISpot reader. The expanded cell populations for each volunteer are examined by flow cytometry to confirm their memory B cell phenotype, i.e. CD19+, CD27+, IgG+, IgM+, CD38+, IgD−.

E. Cellular Immune Responses

Heparinized blood (50 mL cohorts 1 and 2, 25 mL cohort 3) was collected as coded specimens and the peripheral blood mononuclear cells (PBMC) isolated and cryopreserved in liquid nitrogen for possible future evaluation of CMI responses to Norwalk VLP antigen. Assays that may be performed include PBMC proliferative and cytokine responses to Norwalk VLP antigen and can be determined by measuring interferon (IFN)-γ and interleukin (IL)-4 levels according to established techniques.

Example 3

Safety and Immunogenicity Study of Two Dosages of Intranasal Norwalk VLP Vaccine in Humans (LV01-102 Study)

A randomized, double blind, multi-center study in healthy adults was conducted to compare the safety and immunogenicity of two dosage levels (50 µg and 100 µg) of a Norwalk virus-like particle (VLP) vaccine with adjuvant/excipients and placebo controls (empty device). The vaccine consisted of Norwalk virus-like particles (VLPs) in a dry powder matrix designed for intranasal administration as described in Example 2. Vaccinees included healthy adult volunteers ages 18-49 who were H type 1 antigen secretors. Saliva was collected from volunteers to determine H type 1 antigen secretor status. Further, only subjects whose blood type was A or O (not type B or AB) were included in the study as those with B blood type are reported to be less susceptible to Norwalk infection (Glass et al. (2009) N. Engl. J. Med., Vol. 361: 1776-1785). The human volunteers were randomly assigned to one of four groups and each group received one of the following treatments: two 50 µg doses of the Norwalk VLP vaccine (n=20), two 100 µg doses of the Norwalk VLP vaccine (n=20), two doses of the adjuvant/excipient (n=10), or two doses of an air puff placebo (n=11). Volunteers were dosed on days 0 and 21 and were required to keep a 7-day diary of symptoms after each dose. Blood for serology, antibody secreting cells (ASC), and stool and saliva samples for mucosal antibody evaluation were collected.

The components of the vaccine are listed in Table 3 in Example 2. The vaccine was packaged in an intranasal delivery device. Single administrations of the Norwalk VLP vaccine were packaged in a single dose Bespak (Milton Keynes, UK) UniDose DP dry powder intranasal delivery device. Each device delivered 10 mg of the dry powder vaccine formulation. Each dose of vaccine consisted of two delivery devices, one in each nostril. The total vaccine dose was 20 mg of dry power. Therefore, the 50 µg vaccine dose consisted of two devices that each delivered 10 mg of dry powder formulation, wherein each 10 mg of dry powder formulation consisted of 25 µg of Norwalk VLP, 25 µg MPL® adjuvant, 7 mg chitosan, 1.5 mg mannitol, and 1.5 mg sucrose. Similarly, the 100 µg vaccine dose consisted of two devices that each delivered 10 mg of dry powder formulation, wherein each 10 mg of dry powder formulation consisted of 50 µg of Norwalk VLP, 25 µg MPL® adjuvant, 7 mg chitosan, 1.5 mg mannitol, and 1.5 mg sucrose. The formulation of Adjuvant/Excipient was the same as the Norwalk VLP vaccine except that no Norwalk VLP antigen was included in the formulation. The formulation of the Adjuvant/Excipient (also referred to as dry powder matrix) is summarized in Table 4 in Example 2. The placebo group received two empty devices (air puffs).

The volunteers kept a daily diary of symptoms (including local symptoms such as: nasal discharge, nasal pain/discomfort, nasal congestion, runny nose, nasal itching, nose bleed, headache and systemic symptoms such as: daily oral temperature, myalgia, nausea, vomiting, abdominal cramps, diarrhea, and loss of appetite) for 7 days after receiving either one of the two doses of the Norwalk VLP vaccine, dry powder matrix alone, or the placebo. Interim medical histories were obtained at each follow-up visit (days 7±1, 21±2, 28±2, 56±2 and 180±14); volunteers were queried about interim illness, medications, and doctor's visits. Volunteers were asked to report all serious or severe adverse events including events that were not solicited during follow up visits. Volunteers had CBC and serum creatinine, glucose, AST, and ALT assessed on days 7 and 28 (7 days after each immunization) and, if abnormal, the abnormal laboratory test was followed until the test became normal or stabilized.

The safety data were very similar to those described in Table 5 for the study in Example 2. After Dose 1 or Dose 2 of the 100 µg dosage of vaccine local nasal symptoms were reported by 19 of 20 subjects and 18 of 20 subjects, respectively. Likewise in the MPL plus chitosan control group without Norwalk antigen (adjuvant/excipient group), 10 of 10 subjects and 8 of 10 subjects reported local nasal symptoms after Dose 1 or Dose 2, respectively. In the true placebo group, 8 of 11 (73%) subjects and 3 of 11 (27%) subjects who received a puff of air (no dry powder) reported local nasal symptoms after Dose 1 or Dose 2, respectively. Headache and malaise were the most common systemic symptoms observed across the study groups. After Dose 1 or Dose 2 of the 100 µg dosage of vaccine headache was reported in 35% and 47.4% of subjects, respectively. In the adjuvant/excipient (MPL plus chitosan) control group, 30% and 22.2% of subjects reported headache after Dose 1 or Dose 2, respectively. In the true placebo recipients, 36.4% of subjects and 18.2% of subjects reported headache after Dose 1 and Dose 2, respectively.

Clinical laboratory abnormalities were infrequent and observed with similar frequency across the study groups. Severe (Grade 3) hematologic abnormalities were not observed. Two severe (Grade 3) chemistry abnormalities were observed; an elevated AST in a recipient of the 50 µg dosage of vaccine and a decreased glucose in a placebo recipient. One serious adverse event not related to the vaccine was reported in the 180 day safety period; a hospitalization for appendectomy 111 days after the second dose of vaccine. No new onset medically significant medical conditions were reported in the 180 day safety period. These results demonstrate that the Norwalk vaccine containing higher doses of antigen is well tolerated and generally safe in human patients.

To analyze the immunogenicity of the Norwalk vaccine, blood was collected before immunization and on days 7±1, 21±2, 28±2, 56±2, and 180±14 to measure serum antibodies to the Norwalk VLP vaccine by enzyme-linked immunosorbent assays (ELISA). Before and on day 7 after administration of each dose of vaccine, dry powder matrix alone, or placebo, peripheral blood lymphocytes were collected to detect antibody secreting cells by ELISPOT assay. Before and on days 21±2, 56±2 and 180±14 after vaccination, whole blood was obtained to separate cells and freeze for future studies of cell mediated immunity, including cytokine production in response to Norwalk VLP antigen, and lymphoproliferation. Blood was screened for memory B-cells on days 0, 21, 56 and 180.

Methods used to analyze the blood samples collected from immunized individuals, or individuals receiving the dry powder matrix alone or placebo are described in detail in Example 2.

Serum samples were collected before immunization and on days 7, 21, 28, 56, and 180 days after intranasal administration of the first dose of vaccine. The second dose of vaccine was administered on day 21. Purified Norwalk VLPs were used as the target antigen to detect specific serum IgG and IgA endpoint antibody titers determined in comparison to a reference standard curve for each antibody class as previously described (Tacket et al. (2003) Clin. Immunol., Vol. 108:241-247; Gray et al. (1994) J. Clin. Microbiol., Vol. 32:3059-63). Geometric mean titers (GMTs), geometric mean of fold rises (GMFRs) and seroconversion rates (≥4-fold rises) were determined. Norwalk VLP-specific IgG and IgA antibody seroconversion rates and GMFRs are presented in Table 7. No subjects developed ≥4-fold rises in serum IgM antibody. As shown in Table 7, 12 of 19 subjects (63%) in the 100 µg group seroconverted with IgG antibodies at day 56 and 15 of 19 subjects (79%) seroconverted with IgA antibodies. The GMTs pre- and post-vaccination are presented in FIGS. 4C and D. Both vaccine groups (50 and 100 µg) induced strong serum IgA and IgG responses that were significantly higher than the two control groups.

TABLE 7

Anti-Norwalk VLP Specific IgG and IgA Antibody Seroconversion Rates (% ≥4-fold rise) and Geometric Mean Fold Rise (GMFR) by Group at Day 56 (35 Days Post-Vaccination 2) Compared to Baseline Pre-Vaccination

|  | Serum IgG ≥4-fold rise n/N (%) | Serum IgG GMFR | Serum IgA ≥4-fold rise n/N (%) | Serum IgA GMFR |
|---|---|---|---|---|
| 50 µg Norwalk Vaccine | 10/18 (56%) | 4.6 (2.5, 8.6) | 13/18 (72%) | 7.6 (4.2, 13.8) |
| 100 µg Norwalk Vaccine | 12/19 (63%) | 4.8 (3.2, 7.1) | 15/19 (79%) | 9.1 (4.7, 17.6) |
| MPL plus chitosan control (adjuvant/excipient) | 0/9 (0%) | 1.1 (0.9, 1.4) | 0/9 (0%) | 1.0 (0.8, 1.3) |
| Placebo Control | 0/11 (0%) | 0.9 (0.8, 1.1) | 0/11 (0%) | 1.2 (0.9, 1.5) |

Figure 5:
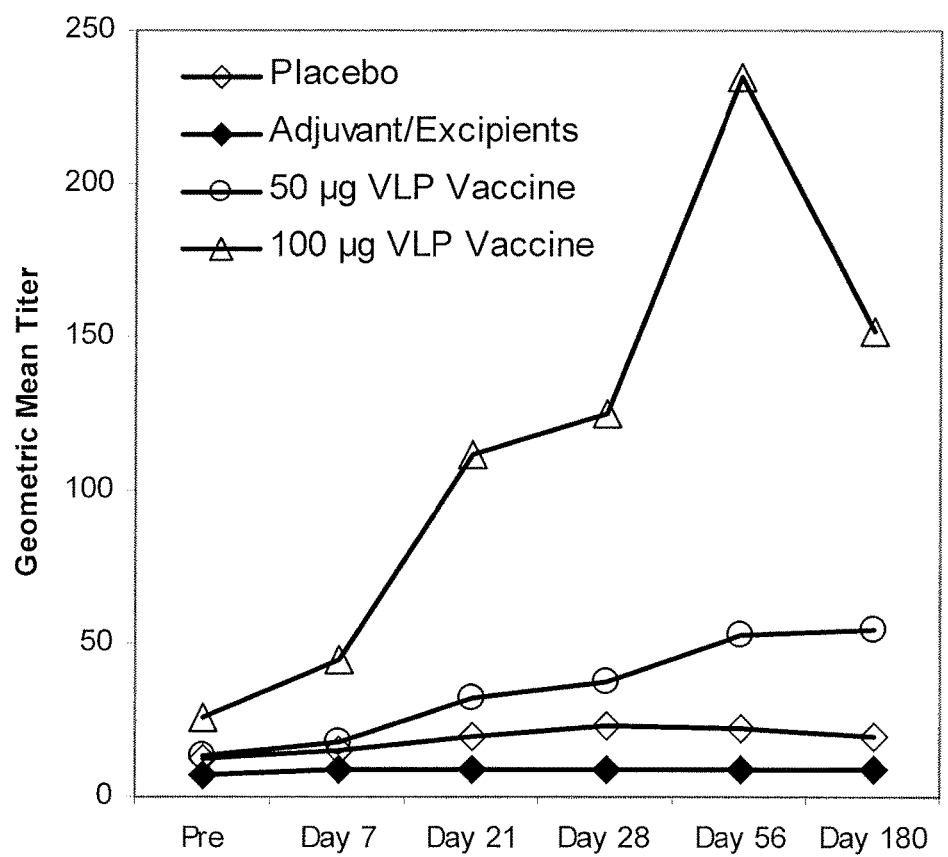
FIG. 5 shows the geometric mean titers for Norwalk VLP-specific hemagglutination inhibition antibody by Group in Study 2 (Example 3). Sixty-one healthy adult subjects were enrolled at four sites and randomized 2:2:1:1, respectively, to receive either two doses of: (1) 50 μg Norwalk VLP vaccine (open circles, n=20); (2) 100 μg Norwalk VLP vaccine (open triangles, n=20); (3) adjuvant control (solid diamonds, n=10); or (4) true placebo (open diamonds, n=11) consisting of a puff of air (no dry powder). All doses were delivered intranasally, and the two-dose regimen was separated by 21 days. The HAI titer represents a measurement of functional antibody levels.

To ascertain the functional antibody response in the various immunization groups, sera was obtained from immunized patients at various points following immunization and analyzed for its ability to inhibit hemagglutination of red blood cells by Norwalk VLPs (a functional assay which indicates protective immune responses) as described in Example 2. Hemagglutination inhibition (HAI) titers were calculated as the inverse of the highest dilution that inhibited hemagglutination, with a compact negative RBC pattern (button of RBCs). The vaccine-induced antibodies were also examined in their capacity to inhibit hemagglutination (HAI) of O-type human RBCs by Norwalk VLP. HAI titers (GMTs, GMFRs and ≥4-fold rises) are presented in Table 8 and the Norwalk-specific GMTs are presented in FIG. 5. Among subjects who received the 100 µg dosage of vaccine, the geometric mean HAI antibody titers peaked after the second dose with a GMFR of 9.1 (CI 4.0, 20.7) and seroconversion occurred in 73.7% of these subjects. The HAI titer can be a good indicator of protective immunity because this measurement reflects the level of functional antibodies that likely block Norovirus entry. The results of these experiments show that the Norovirus vaccine, especially at the 100 µg dosage, can induce a significant HAI titer in humans following immunization suggesting that the vaccine likely induces a protective immunity.

TABLE 8

Specific Hemagglutination Inhibition Antibody Geometric Mean Titers, Geometric Mean Fold Rises, and Seroconversion Rates by Group

| | Baseline (Pre-Vaccination) | | Day 21 (Pre-Vaccination 2) | | | | Day 56 (35 Days Post Vaccination 2) | | | | Day 180 (159 Days Post Vaccination 2) | | | |
|---|---|---|---|---|---|---|---|---|---|---|---|---|---|---|
| | N | GMT (95% CI) | N | GMT (95% CI) | GMFR (95% CI) | % ≥ 4-Fold Rise (95% CI) | N | GMT (95% CI) | GMFR (95% CI) | % ≥ 4-Fold Rise (95% CI) | N | GMT (95% CI) | GMFR (95% CI) | % ≥ 4-Fold Rise (95% CI) |
| 50 μg Norwalk Vaccine | 18 | 13.2 (8.6, 20.1) | 18 | 32.0 (14.9, 68.9) | 2.4 (1.2, 4.8) | 33.3 (13.3, 59.0) | 18 | 52.8 (25.8, 108.2) | 4.0 (2.0, 7.9) | 38.9 (17.3, 64.3) | 17 | 54.4 (25.4, 116.4) | 4.0 (1.9, 8.3) | 47.1 (23.0, 72.2) |
| 100 μg Norwalk Vaccine | 19 | 25.7 (14.7, 44.9) | 19 | 111.9 (41.7, 300.5) | 4.4 (2.1, 9.0) | 63.2 (38.4, 83.7) | 19 | 234.9 (79.7, 692.8) | 9.1 (4.0, 20.7) | 73.7 (48.8, 90.9) | 19 | 151.6 (56.9, 403.9) | 5.9 (2.9, 12.1) | 57.9 (33.5, 79.7) |
| MPL plus Chitosan | 9 | 6.9 (4.1, 11.5) | 9 | 9.3 (5.2, 16.7) | 1.4 (1.0, 1.8) | 0.0 (0.0, 33.6) | 9 | 9.3 (4.7, 18.7) | 1.4 (1.0, 1.8) | 0.0 (0.0, 33.6) | 9 | 8.6 (4.9, 15.2) | 1.3 (0.9, 1.8) | 11.1 (0.3, 48.2) |
| Placebo Control | 11 | 12.4 (5.7, 27.3) | 11 | 19.3 (7.8, 48.0) | 1.6 (0.9, 2.7) | 9.1 (0.2, 41.3) | 11 | 21.9 (8.2, 58.7) | 1.8 (0.9, 3.5) | 9.1 (0.2, 41.3) | 10 | 19.7 (7.7, 50.2) | 1.7 (1.0, 2.9) | 10.0 (0.3, 44.5) |

ASC assays were conducted to detect circulating mononuclear cells secreting IgG and IgA antibodies to Norwalk VLPs (Tacket et al. (2003) Clin. Immunol., Vol. 108:241-247). Twenty-five mL of heparinized blood were collected from each subject on days 0, 7, 21, and 28 (prior to and 7 days after administration of the first and second dose of vaccine or controls). The response rate and mean number of ASCs per $10^6$ peripheral blood mononuclear cells (PBMCs) were assessed. A positive response was defined as a post-vaccination ASC count that consisted of at least >8 spots per $10^6$ PBMCs and was at least 3 standard deviations (SD) above the mean pre-vaccination count for all subjects. Norwalk VLP-specific IgG and IgA circulating ASC were detected at day 7, waned at day 21 (immediately prior to Dose 2), and reappeared at study day 28, seven days after Dose 2 (Table 9). In Study 1 (Example 2), seven (39%) of 18 subjects who were evaluated and received any vaccine dosage developed rises in specific IgA ASC at day 7, and 10 (53%) of 19 subjects had ASC responses at day 28 (Table 9). In this study (Example 3), all 10 subjects evaluated (100%) who received 50 or 100 μg of vaccine developed IgA ASCs at day 7 and at day 28.

TABLE 9

Norwalk VLP-Specific IgA Antibody Secreting Cell (ASC) Response Rate and ASC Geometric Mean Response by Group by Study

| | IgA ASC Response Rate | | | IgA ASC GM of cells per $10^6$ PBMC | | |
|---|---|---|---|---|---|---|
| | Day 7 | Day 21 | Day 28 | Day 7 | Day 21 | Day 28 |
| Study 1 (Example 2) | | | | | | |
| 5 μg Norwalk Vaccine | 0/3 (0%) | 0/5 (0%) | 1/5 (20%) | 0.5 (−) | 0.36 (−) | 0.9 (−) |
| 15 μg Norwalk Vaccine | 0/5 (0%) | 0/5 (0%) | 4/5 (80%) | 0.6 (−) | 0.35 (−) | 12.1 |
| 50 μg Norwalk Vaccine | 7/10 (70%) | 1/10 (10%) | 5/9 (56%) | 9.2 | 1.50 | 8.0 |
| MPL plus Chitosan Control | 0/8 (0%) | 0/8 (0%) | 0/8 (0%) | 0.2 (−) | 0.19 (−) | 0.4 (−) |
| Study 2 (Example 3) | | | | | | |
| 50 μg Norwalk Vaccine | 5/5 (100%) | 0/5 (0%) | 5/5 (100%) | 50.2 | 0.3 (−) | 16.5 |
| 100 μg Norwalk Vaccine | 5/5 (100%) | 1/5 (20%) | 5/5 (100%) | 138.3 | 1.6 | 71.1 |

TABLE 9-continued

Norwalk VLP-Specific IgA Antibody Secreting Cell (ASC) Response Rate and ASC Geometric Mean Response by Group by Study

|  | IgA ASC Response Rate | | | IgA ASC GM of cells per $10^6$ PBMC | | |
| --- | --- | --- | --- | --- | --- | --- |
|  | Day 7 | Day 21 | Day 28 | Day 7 | Day 21 | Day 28 |
| MPL plus Chitosan Control | 0/3 (0%) | 0/3 (0%) | 0/3 (0%) | 0.1 (−) | 0.1 (−) | 0.1 (−) |
| Placebo Control | 0/2 (0%) | 0/2 (0%) | 0/2 (0%) | 0.1 (−) | 0.1 (−) | 0.1 (−) |

The geometric mean pre-administration (Day 0) ASC responses were all <1. The symbol (−) indicates a negative response.

Discussion

Figure 4:
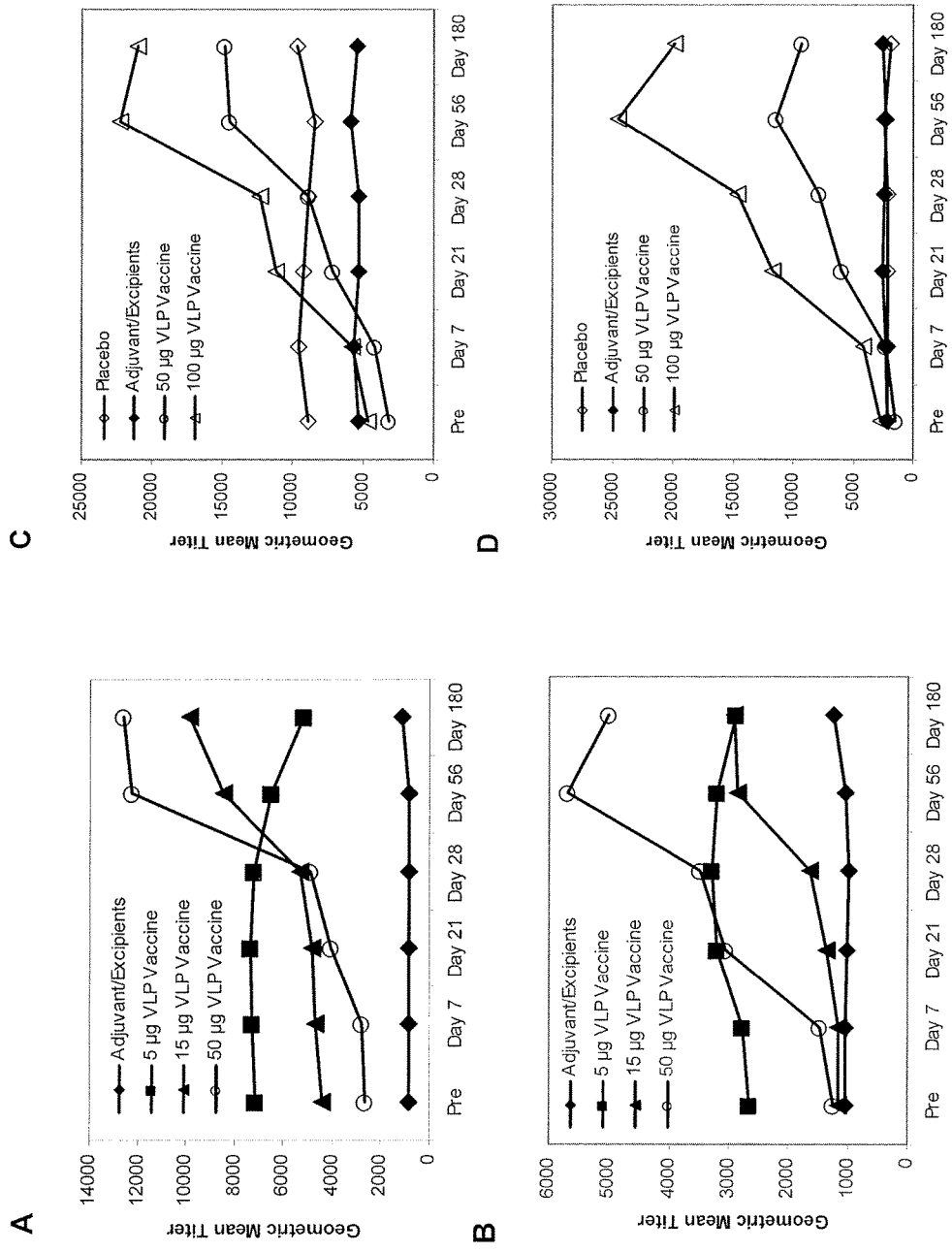
FIG. 4 shows Norwalk VLP-Specific IgG and IgA Geometric Mean Antibody Titers by Group by Study. In Study 1 (Example 2), twenty-eight adult subjects were randomized sequentially by group to receive two doses of: (1) 5 μg Norwalk VLP vaccine (solid squares, n=5) or adjuvant control (solid diamonds, n=2); (2) 15 μg Norwalk VLP vaccine (solid triangles, n=5) or adjuvant control (n=2); or (3) 50 μg Norwalk VLP vaccine (open circles, n=10) or adjuvant control (n=4). (A) Serum IgG geometric mean titers from Study 1 (Example 2); (B) Serum IgA geometric mean titers from Study 1 (Example 2). In Study 2 (Example 3), sixty-one healthy adult subjects were enrolled at four sites and randomized 2:2:1:1, respectively, to receive either two doses of: (1) 50 μg Norwalk VLP vaccine (open circles, n=20); (2) 100 μg Norwalk VLP vaccine (open triangles, n=20); (3) adjuvant control (solid diamonds, n=10); or (4) true placebo (open diamonds, n=11) consisting of a puff of air (no dry powder). (C) Serum IgG geometric mean titers from Study 2; (D) Serum IgA geometric mean titers from Study 2 (Example 3). All doses were delivered intranasally, and the two-dose regimen was separated by 21 days.

Norwalk VLP-specific IgG and IgA seroconversion rates and GMFRs are presented in Table 10, and the kinetics of antibody production (GMTs before and after vaccination) are presented in FIG. 4. In Study 1 (Example 2), the seroconversion rates showed a dose-dependent response with increased titers as the dosage of vaccine antigen increased; a logistic regression with dose as a continuous variable results in a chi-sq p-value<0.01 for IgG seroconversion rates and a chi-sq p-value<0.02 for IgA seroconversion rates. In Study 2 (Example 3), 12 (63%) of 19 subjects in the 100 μg group seroconverted for IgG antibodies and 15 (79%) of 19 subjects seroconverted for IgA antibodies at day 56 (Table 10). The 100 μg group developed higher titers than the 50 μg group but the differences were not statistically significant. Both vaccine groups developed higher serum IgG and IgA responses than the two control groups; a logistic regression with dose as a continuous variable results in a chi-sq p-value<0.001 for IgG and IgA seroconversion rates. No subjects developed ≥4-fold rises in serum IgM antibody (data not shown).

observed 7 days after the first dose of the 100 μg dosage of vaccine in all five subjects evaluated with a geometric mean of 138 cells/$10^6$ peripheral blood mononuclear cells. These numbers are higher than what was previously observed after administration of oral non-adjuvanted Norwalk VLP vaccine or after ingestion of non-adjuvanted Norwalk VLP antigen in edible transgenic plants (Tacket et al. (2003) Clin. Immunol., Vol. 108:241-247; Tacket et al. (2000) J. Infect. Dis., Vol. 182:302-305). These ASC counts are also relatively higher when compared to those induced by oral vaccines as well as to wild-type challenges with enteric organisms (Tacket et al. (2003) Clin. Immunol., Vol. 108:241-247; Kotloff et al. (2001) Infec. Immun., Vol. 69:3581-3590; Kotloff et al. (2000) Infect. Immun., Vol. 68:1034-1039; McKenzie et al. (2007) Vaccine, Vol. 25:3684-3691; and Kotloff et al. (2007) Human Vaccines, Vol. 3:268-275).

ASC were observed in the circulation 7 days after immunization. To investigate the expression of homing molecules known to direct their migration to mucosal and peripheral lymphoid tissues, PBMCs from 5 subjects were stained and sorted simultaneously into 4 defined subsets and assessed for

TABLE 10

Norwalk VLP-Specific IgG and IgA Antibody Seroconversion Rates (percent of subjects with ≥4-fold rise) and Geometric Mean Fold Rise (GMFR) by Group by Study at Day 56 (35 Days Post-Vaccination 2) Compared to Pre-Vaccination

|  | Serum IgG ≥4-fold rise n/N (%) | Serum IgG GMFR | Serum IgA ≥4-fold rise n/N (%) | Serum IgA GMFR |
| --- | --- | --- | --- | --- |
| Study 1 (Example 2) | | | | |
| 5 μg Norwalk Vaccine | 0/5 (0%) | 0.9 | 0/5 (0%) | 1.2 |
| 15 μg Norwalk Vaccine | 2/5 (40%) | 1.9 | 2/5 (40%) | 2.5 |
| 50 μg Norwalk Vaccine | 7/9 (78%) | 4.7 | 5/9 (56%) | 4.5 |
| MPL plus chitosan control | 1/8 (13%) | 1.0 | 0/8 | 1.0 |
| Study 2 (Example 3) | | | | |
| 50 μg Norwalk Vaccine | 10/18 (56%) | 4.6 (2.5, 8.6) | 13/18 (72%) | 7.6 (4.2, 13.8) |
| 100 μg Norwalk Vaccine | 12/19 (63%) | 4.8 (3.2, 7.1) | 15/19 (79%) | 9.1 (4.7, 17.6) |
| MPL plus chitosan control | 0/9 (0%) | 1.1 (0.9, 1.4) | 0/9 (0%) | 1.0 (0.8, 1.3) |
| Placebo Control | 0/11 (0%) | 0.9 (0.8, 1.1) | 0/11 (0%) | 1.2 (0.9, 1.5) |

The immunogenicity of the adjuvanted Norwalk VLP vaccine as measured by serum IgG and IgA antibodies and circulating Norwalk IgG and IgA specific ASCs is notable. Mucosal priming via the nasal mucosa was supported by the ASC responses in the peripheral blood. ASCs appear transiently in the circulation after naïve B lymphocytes at an inductive site are exposed to antigen (e.g., nasal associated lymphoid tissue). ASCs return to the mucosa as immune effector cells. Norwalk IgA-specific ASC responses were their ability to secrete Norwalk IgG and IgA as described above (Table 11). The majority of IgA ASCs were observed in two main subsets: CD19+ CD27+ CD62L+, integrin α4/β7+, i.e., expressing both peripheral lymphoid tissue and mucosal homing molecules (~700 to ~10,700 ASC/$10^6$ sorted cells); and CD19+ CD27+ CD62L− integrin α4/β7+, i.e., expressing exclusively mucosal homing molecules (~2,500 to ~6,700 ASC/$10^6$ sorted cells). The latter was observed in 3 of 4 vaccinees (Table 11).

TABLE 11

Norwalk VLP Specific IgA and IgG Cell Surface Receptor Homing Markers

| Group | P* | N/MB* | M/P* | M* |
|---|---|---|---|---|
| IgA (total # of cells/10$^6$) | | | | |
| Placebo | 0 | 0 | 0 | 4 |
| 50 μg Vaccine | 0 | 2 | 1,000 | 5,197 |
| 100 μg Vaccine | 95 | 14 | 1,999 | 2,666 |
| 100 μg Vaccine | 33 | 0 | 717 | 0 |
| 100 μg Vaccine | 0 | 15 | 10,739 | 6,668 |
| IgG (total # of cells/10$^6$) | | | | |
| Placebo | 0 | 0 | 0 | 4 |
| 50 μg Vaccine | 0 | 0 | 450 | 742 |
| 100 μg Vaccine | 0 | 0 | 157 | 0 |
| 100 μg Vaccine | 0 | 0 | 282 | 0 |
| 100 μg Vaccine | 0 | 0 | 667 | 0 |
| Sorted subpopulation phenotype | | | | |
| P*—Peripheral homing memory B/plasma cell | CD19+ | CD19+ | CD19+ | CD19+ |
| N/MB*—Naïve mature B cell | CD27+ | CD27− | CD27+ | CD27+ |
| M/P*—Mucosal and peripheral homing memory B/plasma cell | CD62L+ | | CD62L+ | CD62L− |
| M*—Mucosal homing memory B/plasma cell | α4β7− | | α4β7+ | α4β7+ |

In contrast, the IgG ASC, with the exception of 1 vaccinee, were of a single phenotype: CD19+ CD27+ CD62L+ integrin α4/β7+, and the frequencies (~150 to ~670 ASC/10$^6$ sorted cells) were considerably lower than those observed for IgA ASC. One vaccinee dosed at the 50 μg level exhibited IgG ASC subsets bearing both mucosal and peripheral lymphoid tissues homing receptors (Table 11).

No IgG or IgA ASC exhibited a phenotype associated with either naïve B cells (CD19+, CD27−) or B$_M$ (CD19+, CD27+) cells expressing CD62L in the absence of integrin α4/β7, which would presumably home exclusively to peripheral lymphoid tissues.

The intranasal monovalent adjuvanted Norwalk VLP vaccine was generally well tolerated and immunogenic. A second dose of vaccine provided increased serologic antibody responses whereas the peak increase in ASC responses occurred after Dose 1. HAI antibody (a functional measurement) increased only at the highest dosage tested and the fold increase (9-fold) was similar to that of the serum IgA. Mucosal priming via the nasal mucosa was supported by the presence of high frequencies of IgA and IgG ASCs in peripheral blood. ASCs appear transiently in the circulation after naïve B lymphocytes at an inductive site are exposed to a foreign antigen (e.g., vaccine-primed B cells at the nasal associated lymphoid tissue return to the mucosa as immune effector cells). Norwalk IgA-specific ASC responses were observed 7 days after the first immunization in all five subjects that received the 100 μg vaccine dose, with a geometric mean of 138 cells/10$^6$ PBMCs. The ASC numbers reported in this study are higher than what has been previously observed after administration of oral non-adjuvanted Norwalk VLP vaccine or after ingestion of non-adjuvanted Norwalk VLP antigen in edible transgenic plants (Tacket et al. (2003) Clin Immunol., Vol. 108:241-7; and Tacket et al. (2000) J. Infect. Dis., Vol. 182:302-305). These ASC counts are also generally higher than those induced by live oral vaccines or by wild-type challenges with enteric organisms (Tacket et al. (2003) Clin Immunol., Vol. 108:241-7; Kotloff et al. (2001) Infec. Immun., Vol. 69:3581-3590; Kotloff et al. (2000) Infect. Immun., Vol. 68:1034-1039; McKenzie et al. (2007) Vaccine, Vol. 25:3684-3691; and Kotloff et al. (2007) Human Vaccines, Vol. 3:268-275). Thus, these mucosally-primed ASCs in combination with the serum IgG and IgA antibodies may contribute to protection. Graham et al. (J Infect Dis, Vol. 170:34-43, 1994) reported a 35-fold mean increase in serum antibody titers in a population of 41 Norwalk virus infected subjects following virus challenge. Gray et al. (J Clin Microbiol, Vol. 32:3059-63, 1994) evaluated a subset of these sera for IgG and IgA by ELISA and observed Norwalk IgG peak titers of approximately 15,900 from days 15 to 90 and IgA peak titers of approximately 12,600 from days 24 and 90. A comparison of IgG and IgA between challenged and vaccinated subjects is planned.

These results show for the first time the presence of circulating Norwalk-specific IgA and IgG ASC following intranasal vaccination with adjuvanted VLP. Hence, it was important to study the homing characteristics of these effector cells. It is widely accepted that CD62L is a key molecule implicated in the initial phase of migration through high endothelial venules (HEV) in lymphoid tissues, including lymph nodes and Peyer's Patches, through binding to the peripheral lymph node addressins (PNad) and the mucosal addressin cell adhesion molecule (MAdCAM-1) present in the HEV vascular endothelium, which results in tethering and rolling (Brandtzaeg et al. (2005) Immunol Rev, Vol. 206:32-63; Bargatze et al. (1995) Immunity, Vol. 3:99-108; and Shyjan et al. (1996) J. Immunol., Vol. 156:2851-7). In contrast, at mucosal effector sites, although a number of adhesion molecules are involved, vascular adhesion specificity is mediated by integrin α4/β7 interacting with the MAdCAM-1 addressin (Brandtzaeg et al. (2005) Immunol Rev, Vol. 206:32-63; Bargatze et al. (1995) Immunity, Vol. 3:99-108; and Shyjan et al. (1996) J. Immunol., Vol. 156: 2851-7). Thus, cells expressing integrin α4/β7, but not CD62L, are destined to home to the gut mucosa, whilst cells expressing CD62L, but not integrin α4/β7, are destined to home to peripheral and mesenteric lymph nodes. As an example, a previous study evaluating B cell surface markers in response to acute rotavirus infections showed that cells homing to the gut mucosa were CD27+ integrin α4/β7+ CD62L+/− (Jaimes et al. (2004) J. Virol., Vol. 78:10967-10976).

We observed that intranasal immunization with an adjuvanted Norovirus VLP vaccine elicited circulating VLP-specific IgA and IgG ASC with different homing potentials. While IgA specific ASC exhibited homing receptors likely to endow them with the ability to home to both, the gut mucosa (CD19+ CD27+ integrin α4/β7+ CD62L−) and peripheral lymphoid tissues (CD19+ CD27+ integrin α4/β7+ CD62L+), IgG ASC expressed homing receptors that support homing to peripheral lymphoid tissues (CD19+ CD27+ integrin α4/β7+ CD62L+). The fact that intranasal immunization was able to elicit ASC with such diverse homing profile, including the gut mucosa, is noteworthy and demonstrates that this route has the capacity to induce potent systemic and mucosal immune responses, including effector cells active at a distant site of infection (i.e. the gastrointestinal tract in the case of Norovirus virus). However, intranasal immunization was not effective in inducing significant levels of specific IgG or IgA ASC with the potential to home exclusively to peripheral lymphoid tissues (Brandtzaeg et al. (2005) Immunol Rev, Vol. 206:32-63).

Example 4

Norwalk Virus Challenge Study in Humans Immunized with Norwalk Virus VLP Vaccine Formulation (LV01-103 Study)

A multi-site, randomized, double-blind, placebo-controlled Phase 1-2 challenge study was conducted in 80 human volunteers immunized with the Norwalk VLP vaccine described in Example 2 above. Eligible subjects included those 18-50 years of age, in good health, who express the H type-1 oligosaccharide (as measured by positive salivary secretor status) and who are other than Type B or AB blood type. Subjects who are non H type-1 secretors or who have Type B or AB blood are reported to be more resistant to infection with Norwalk virus and were excluded from the study. At least 80% of volunteers were expected to be eligible based on these two criteria.

Following screening, eligible volunteers who meet all acceptance criteria were randomized (1:1) into one of two equal sized cohorts with approximately 40 volunteers in each cohort. Cohort 1 is immunized with Norwalk VLP and cohort 2 receives placebo. Volunteers were immunized with 10 mg Norwalk VLP vaccine in each nostril (20 mg total dry powder) or placebo. Each 10 mg of Norwalk VLP vaccine contained 50 µg of Norwalk VLP, 7 mg chitosan, 25 µg MPL®, 1.5 mg of sucrose and approximately 1.5 mg of mannitol. Thus, each volunteer in cohort 1 received a total dosage of 100 µg of Norwalk VLP antigen at each immunization. Volunteers received vaccine or placebo on study days 0 and 21.

The safety of the Norwalk virus VLP vaccine compared to placebo was assessed. Volunteers kept a diary for 7 days following each immunization with the vaccine or placebo to document the severity and duration of adverse events. Serious adverse events (SAEs) and the occurrence of any significant new medical conditions was followed for 6 months after the last dose of vaccine or placebo and for 4 months after the challenge with infectious virus.

All volunteers were challenged with infectious Norwalk virus between 21 to 42 days after the second dose of vaccine or placebo (between study days 42 and 56). Each volunteer received at or > than the 50% Human Infectious Dose (HID 50), i.e. the amount of infectious virus that is expected to cause disease in at least 50% of volunteers in the placebo group. The HID 50 is between about 48 and about 480 viral equivalents of the Norwalk virus. The Norwalk virus was mixed with sterile water and given orally. The inoculation was preceded by ingestion of 500 mg sodium bicarbonate in water, to prevent breakdown of the virus by stomach acid and pepsin. A second ingestion of sodium bicarbonate solution (500 mg sodium bicarbonate in water) was taken 5 minutes after oral inoculation of the infectious virus. The volunteers remained at the challenge facility for at least 4 days and at least 18 hours after symptoms/signs of acute gastroenteritis (vomiting, diarrhea, loose stool, abdominal pain, nausea, and fever) were absent.

Several metrics were monitored to determine the efficacy of the Norwalk VLP vaccine in preventing or reducing symptoms/signs of acute gastroenteritis induced by the viral challenge. All volunteers recorded their clinical symptoms of acute gastroenteritis and these symptoms were documented by the research staff at the study sites. Disease symptoms/signs from cohort 1 receiving the vaccine were compared to cohort 2 placebo recipients.

Sera, saliva, and stool samples were routinely collected from all volunteers prior to immunization with the vaccine or placebo, and after challenge. Serum samples were analyzed by ELISA for IgA and IgG, titers against the Norwalk VLPs. Serum samples were also analyzed for carbohydrate blocking activity by hemagglutination inhibition (HAI) assay. The Norwalk antigen and Norwalk RNA were tested in stool samples by ELISA and PCR, respectively, which indicate the presence of virus, the amount of virus shed from the intestines, and the duration of viral shedding. Subjects who became ill after challenge, were subject to additional laboratory studies including serum chemistries, BUN, creatinine, and liver function tests until symptoms/signs resolved.

Methods of collecting and analyzing the serum samples are similar to those described in Example. Methods of collecting and analyzing the saliva and stool samples are described below.

Collections of Stool and Saliva for Anti-Norwalk VLP sIgA

Anti-recombinant Norwalk Virus IgA is measured in stool and saliva samples. Saliva specimens are treated with protease inhibitors (i.e. AEBSF, leupeptin, bestatin, and aprotinin) (Sigma, St. Louis, Mo.), stored at −70° C., and assayed using a modification of a previously described assay (Mills et al. (2003) Infect. Immun. 71: 726-732). Stool was collected before vaccination and after viral challenge, and specimens were stored at −70° C. until analysis. The specimens are thawed, and protease inhibitor buffer added to prepare a 10% w/v stool suspension. Stool supernatants are assayed for recombinant Norwalk Virus (rNV)-specific mucosal IgA by ELISA, as described below.

Approximately 2-3 mL of whole saliva was collected before vaccination and after viral challenge. Saliva was collected by a commercially available device (Salivette, Sarstedt, Newton, N.C.), in which a Salivette swab is chewed or placed under the tongue for 30-45 seconds until saturated with saliva. Saliva was collected from the swab by centrifugation.

Measurement of Anti-Norwalk VLP in Stool and Saliva

ELISAs, utilizing plates coated with either anti-human IgA antibody reagents or target rNV VLP antigen coatings, are performed to determine total IgA and to titer the specific anti-VLP IgA responses for each specimen. Total or specific IgA are revealed with HRP-labeled anti-human IgA as described above. An internal total IgA standard curve is included to quantify the IgA content. Response is defined as a 4-fold rise in specific antibody.

Results from the vaccine group (cohort 1) and the placebo group (cohort 2) are compared to assess the protective efficacy of the vaccine against Norovirus disease overall (primary endpoint), and/or its efficacy in ameliorating the symptoms/signs (severity and # of days of illness) and/or the reduction of the presence, the amount and/or the duration of virus shedding (secondary endpoints).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

REFERENCES

1. Glass, R I, J S Noel, T Ando, R L Fankhauser, G Belloit, A Mounts, U D Parasher, J S Bresee and S S Monroe. The Epidemiology of Enteric Caliciviruses from Human: A Reassessment Using New Diagnostics. *J Infect Dis* 2000; 181 (Sup 2): S254-S261.
2. Hardy, M E. Norwalk and "Norwalk-like Viruses" in Epidemic Gastroenteritis. *Clin Lab Med* 1999; 19(3): 675-90.
3. Jiang, X, D Y Graham, K N Wang, and M K Estes. Noralk Virus Genome Cloning and Characterization. *Science* 1990; 250: 1580-1583.
4. Jiang, X, M Want, D Y Graham, and M K Estes. Expression, Self-Assembly, and Antigenicity of the Norwalk Virus Capsid Protein. *J Virol* 1992; 66: 6527-6532.
5. Glass, P, L J White, J M Ball, I Leparc-Goffart, M E Hardy, and M K Estes. Norwalk Virus Open Reading Frame 3 Encodes a Minor Structural Protein. *J Virol* 2000; 74: 6581-6591.
6. Lindesmith, L, C Moe, S Marionneau, N Ruvoen, X Jiang, L Lindblad, P Stewart, J LePendu, and R Baric. Human Susceptiblity and Resistance to Norwalk Virus Infection. *Nat Med* 2003; 9: 548-553.
7. Parrino, T A, D S Schreiber, J S Trier, A Z Kapikian, and N R Blacklow. Clinical Immunity in Acute Gastroenteritis Caused by Norwalk Agent. *N Engl J Med* 1977; 297: 86-89.
8. Wyatt, R G, R Dolin, N R Blacklow, H L DuPont, R F Buscho, T S Thornhill, A Z Kapikian, and R M Chanock. Comparison of Three Agents of Acute Infectious Nonbacterial Gastroenteritis by Cross-challenge in Volunteers. *J Infect Dis* 1974; 129: 709.
9. Ball, J M, D Y Graham, A R Opekum, M A Gilger, R A Guerrero, and M K Estes. Recombinant Norwalk Virus-like Particles Given Orally to Volunteers: Phase I Study. *Gastroenterology* 1999; 117: 40-48.
10. Tacket, C O, M B Sztein, G A Losonky, S S Wasserman, and M K Estes. Humoral, Mucosal, and Cellular Immune Responses to Oral Nowalk Virus-like Particles in Volunteers. *Clin Immunol* 2003; 108: 241.
11. Guerrero, R A, J M Ball, S S Krater, S E Pacheco, J D Clements, and M K Estes. Recombinant Norwalk Virus-like Particles Administered Intranasally to Mice Induce Systemic and Mucosal (Fecal and Vaginal) Immune Responses. *J Virol* 2001; 75: 9713.
12. Nicollier-Jamot, B, A Ogier, L Piroth, P Pothier, and E Kohli. Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. *Vaccine* 2004; 22:1079-1086.
13. Periwal, S B, K R Kourie, N Ramachandaran, S J Blakeney, S DeBruin, D Zhu, T J Zamb, L Smith, S Udem, J H Eldridge, K E Shroff, and P A Reilly. A Modified Cholera Holotoxin CT-E29H Enhances Systemic and Mucosal Immune Responses to Recombinant Norwalk Virus-like Particle Vaccine. *Vaccine* 2003; 21: 376-385.
14. Isaka, M, Y Yasuda, S Kozuka, T Taniguchi, K Matano, J Maeyama, T Komiya, K Ohkuma, N Goto, and K Tochikubo. Induction of systemic and mucosal antibody responses in mice immunized intranasally with aluminium-non-adsorbed diphtheria toxoid together with recombinant cholera toxin B subunit as an adjuvant. *Vaccine* 1999; 18: 743-751.
15. Kozlowski, P A, S Cu-Uvin, M R Neutra, and T P Flanigan. Comparison of the oral, rectal, and vaginal immunization routes for induction of antibodies in rectal and genital tract secretions of women. *Infect Immun* 1997; 65: 1387-1394.
16. Mestecky, J, S M Michalek, Z Moldoveanu, and M W Russell. Routes of immunization and antigen delivery systems for optimal mucosal immune responses in humans. *Behring Inst Mitt* 1997; 33-43.
17. Wu, H Y, and M W Russell. Nasal lymphoid tissue, intranasal immunization, and compartmentalization of the common mucosal immune system. *Immunol Res* 1997; 16: 187-201.
18. Evans, J T, C W Cluff, D A Johnson, M J Lacy, D H Persing, and J R Baldridge. Enhancement of antigen-specific immunity via the TLR4 ligands MPL adjuvant and Ribi 529. *Expert Rev Vaccines* 2003; 2: 219-229.
19. Baldridge, J R, Y Yorgensen, J R Ward, and J T Ulrich. Monophosphoryl lipid A enhances mucosal and systemic immunity to vaccine antigens following intranasal administration [In Process Citation]. *Vaccine* 2000; 18: 2416-2425.
20. Yang, Q B, M Martin, S M Michalek, and J. Katz. Mechanisms of monophosphoryl lipid A augmentation of host responses to recombinant HagB from *Porphyromonas gingivalis*. *Infect Immun* 2002; 70: 3557-3565.
21. Baldrick, P, D Richardson, G Elliott, and A W Wheeler. Safety evaluation of monophosphoryl lipid A (MPL): an immunostimulatory adjuvant. *Regul Toxicol Pharmacol* 2002; 35: 398-413.
22. Baldridge, J R, P McGowan, J T Evans, C Cluff, S Mossman, D Johnson, and D Persing. Taking a toll on human disease: Toll-like receptor 4 agonists as vaccine adjuvants and monotherapeutic agents. *Expert Opin Biol Ther* 2004; 4: 1129-1138.
23. Persing, D H, R N Coler, M J Lacy, D A Johnson, J R Baldridge, R M Hershberg, and S G Reed. Taking toll: lipid A mimetics as adjuvants and immunomodulators. *Trends Microbiol* 2002; 10: S32-37.
24. Illum, L. Nasal drug delivery—possibilities, problems and solutions. *J Control Release* 2003; 87: 187-198.
25. Illum, L, I Jabbal-Gill, M Hinchcliffe, A N Fisher, and S S Davis. Chitosan as a novel nasal delivery system for vaccines. *Adv Drug Deliv Rev* 2001; 51: 81-96.
26. Davis, S S. Delivery of peptide and non-peptide drugs through the respiratory tract. *Pharm Sci Technol Today* 1999; 2: 450-456.
27. Bacon, A, J Makin, P J Sizer, I Jabbal-Gill, M Hinchcliffe, L Illum, S Chatfield, and M Roberts. Carbohydrate biopolymers enhance antibody responses to mucosally delivered vaccine antigens. *Infect Immun* 2000; 68: 5764-5770.
28. van der Lubben, I M, J C Verhoef, G Borchard, and H E Junginger. Chitosan for mucosal vaccination. *Adv Drug Deliv Rev* 2001; 52: 139-144.

29. van der Lubben, I M, J C Verhoef, G Borchard, and H E Junginger. Chitosan and its derivatives in mucosal drug and vaccine delivery. *Eur J Pharm Sci* 2001; 14: 201-207.
30. Lim, S T, B Forbes, G P Martin, and M B Brown. In vivo and in vitro characterization of novel microparticulates based on hyaluronan and chitosan hydroglutamate. *AAPS Pharm Sci Tech* 2001; 2: 20.
31. Jabbal-Gill, I, A N Fisher, R Rappuoli, S S Davis, and L Illum. Stimulation of mucosal and systemic antibody responses against *Bordetella pertussis* filamentous haemagglutinin and recombinant *pertussis* toxin after nasal administration with chitosan in mice. Vaccine 1998; 16: 2039-2046.
32. Mills, K H, C Cosgrove, E A McNeela, A Sexton, R Giemza, I Jabbal-Gill, A Church, W Lin, L Illum, A Podda, R Rappuoli, M Pizza, G E Griffin, and D J Lewis. Protective levels of diphtheria-neutralizing antibody induced in healthy volunteers by unilateral priming-boosting intranasal immunization associated with restricted ipsilateral mucosal secretory immunoglobulin. *A Infect Immun* 2003; 71: 726-732.
33. McNeela, E A., I Jabbal-Gill, L Ilium, M Pizza, R Rappuoli, A Podda, D J Lewis, and K H Mills. Intranasal immunization with genetically detoxified diphtheria toxin induces T cell responses in humans: enhancement of Th2 responses and toxin-neutralizing antibodies by formulation with chitosan. *Vaccine* 2004; 22: 909-914.
34. Mikszta, J A., V J Sullivan, C Dean, A M Waterston, J B Alarcon, J P Dekker, 3rd, J M Brittingham, J Huang, C R Hwang, M Ferriter, G Jiang, K Mar, K U Saikh, B G Stiles, C J Roy, R G Ulrich, and N G Harvey. Protective immunization against inhalational anthrax: a comparison of minimally invasive delivery platforms. *J Infect Dis* 2005; 191: 278-288.
35. Huang, J, R J Garmise, T M Crowder, K Mar, C R Hwang, A J Hickey, J A Mikszta, and V J Sullivan. A novel dry powder influenza vaccine and intranasal delivery technology: induction of systemic and mucosal immune responses in rats. *Vaccine* 2004; 23: 794-801.
36. GSK Press Room. www.gsk.com/media/archive.htm
37. Corixa Press Room. www.corixa.com/default.asp?pid=release_detail&id=248&year=2004
38. BioMira Web Site. http://www.biomira.com/business/outLicensing/

The invention claimed is:

1. A method of eliciting protective immunity against Norovirus in a human comprising the steps of:
   (i) intramuscularly administering to the human a vaccine comprising Norovirus virus-like particles (VLPs), wherein the Norovirus VLPs are present in the vaccine in an amount of 1 µg to 200 µg, wherein the vaccine comprises at least one adjuvant that is not a bacterially-derived exotoxin adjuvant, and wherein the administration of the vaccine elicits production of Norovirus-specific functional antibodies in a blood sample from the human; and
   (ii) measuring the Norovirus-specific functional antibodies in the blood sample from the human, wherein a geometric mean serum titer of the Norovirus-specific functional antibodies greater than 40 as measured by a carbohydrate blocking assay is indicative of protective immunity.

2. The method of claim 1, further comprising measuring IgA and/or IgG Norovirus-specific antibody secreting cells in a blood sample from the human.

3. The method of claim 2, wherein the IgA or IgG Norovirus-specific antibody secreting cells are CD19+, CD27+, α4β7+, and either CD62L+ or CD62L−.

4. The method of claim 2, wherein protective immunity comprises an increase in the level of IgA-specific antibody secreting cells in the blood as compared to the level in the human before receiving the vaccine.

5. The method of claim 4, wherein said IgA-antibody secreting cells are CD19+, CD27+, α4β7+, and either CD62L+ or CD62L−.

6. The method of claim 1, wherein the blood sample is obtained at least seven days following administration of the Norovirus vaccine.

7. The method of claim 1, wherein a geometric mean serum titer of Norovirus-specific functional antibodies greater than 100 as measured by a hemagglutination inhibition assay is indicative of protective immunity.

8. The method of claim 1, wherein a geometric mean serum titer of Norovirus-specific functional antibodies greater than 200 as measured by a hemagglutination inhibition assay is indicative of protective immunity.

9. The method of claim 1, wherein said at least one adjuvant is selected from the group consisting of toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, and liposomes.

10. The method of claim 1, wherein the adjuvant is MPL.

11. The method of claim 1, wherein the carbohydrate blocking assay is the hemagglutinin inhibition assay (HAI).

12. The method of claim 1, wherein the Norovirus VLPs are from two or more different Norovirus strains, and wherein the content of at least one Norovirus VLP in the vaccine is 15 µg.

13. The method of claim 1, wherein the Norovirus VLPs are from two or more different Norovirus strains, and wherein the content of at least one Norovirus VLP in the vaccine is 50 µg.

* * * * *